(12) United States Patent
Parkin et al.

(10) Patent No.: US 8,481,284 B2
(45) Date of Patent: Jul. 9, 2013

(54) PROCESS OF PREPARING CONJUGATES OF ALLIUM ORGANOSULFUR COMPOUNDS WITH AMINO ACIDS, PEPTIDES, AND PROTEINS

(75) Inventors: Kirk L. Parkin, Middleton, WI (US); Guodong Zhang, Davis, CA (US)

(73) Assignee: Wisconsin Alumni Research Foundation, Madison, WI (US)

(*) Notice: Subject to any disclaimer, the term of this patent is extended or adjusted under 35 U.S.C. 154(b) by 196 days.

(21) Appl. No.: 12/898,006

(22) Filed: Oct. 5, 2010

(65) Prior Publication Data

US 2011/0082282 A1 Apr. 7, 2011

Related U.S. Application Data

(60) Provisional application No. 61/249,315, filed on Oct. 7, 2009.

(51) Int. Cl.
*C12P 1/00* (2006.01)
*C12P 21/00* (2006.01)
*C07K 1/00* (2006.01)
*C07C 331/00* (2006.01)

(52) U.S. Cl.
USPC ............. 435/41; 435/68.1; 530/408; 560/310

(58) Field of Classification Search
None
See application file for complete search history.

(56) References Cited

U.S. PATENT DOCUMENTS

| | | | |
|---|---|---|---|
| 3,686,324 A * | 8/1972 | Brodnitz et al. ............... | 426/535 |
| 3,723,135 A * | 3/1973 | Pascall et al. .................. | 426/533 |
| 5,244,794 A * | 9/1993 | Prince et al. ................... | 435/113 |
| 6,689,588 B1 | 2/2004 | Mirelman et al. | |
| 2002/0012639 A1 | 1/2002 | Glenn, Jr. et al. | |
| 2005/0260250 A1 | 11/2005 | Ott | |

OTHER PUBLICATIONS

Morimitsu et al., J. Agric. Food Chem. 1992, 40, 368-372.*
International Search Report and Written Opinion of the International Searching Authority received in PCT/US10/51454, dated Dec. 3, 2010.
Shen et al., "In Vitro Biogeneration of Pure Thiosulfinates and Propanthial-S-oxide," J. Agric. Food Chem. 48: 6254-6260 (2000).
Steinmetz and Potter, "Vegetables, fruit, and cancer prevention: a review," J. Am. Diet. Assoc. 96(10):1027-39 (Oct. 1996).
Ernst, C.B., "Current therapy for infrarenal aortic aneurysms," N. Engl. J. Med. 336(1):59-60 (Jan. 1997).
Bianchini, F. and Vainio, H., "Allium Vegetables and Organosulfur Compounds: Do they Help Prevent Cancer?" Environmental Health Perspectives 109:893-902 (Sep. 2001).
Tapiero, H., Townsend D.M. and Tew K.D., "Organosulfur compounds from alliaceae in the prevention of human pathologies," Biomed. Pharmacother. 58(3):183-93 (Apr. 2004).
Lawson, L.D., "Effect of garlic on serum lipids," JAMA. 280(18):1568 (Nov. 1998).
Lawson, L.D. and Wang, Z.J., "Allicin and allicin-derived garlic compounds increase breath acetone through allyl methyl sulfide: use in measuring allicin bioavailability," J. Agric. Food Chem. 53(6):1974-83 (Mar. 2005).
Schwimmer, S. Source Book of Food Enzymology, AVI Publishing Co., Westport, pp. 373-381 (1981).
Wittstock, U. and Burow, M., "Critical Review: Tipping the Scales—Specifier Proteins in Glucosinolate Hydrolysis," IUBMB Life 59(12):744-751 (Dec. 2007).
Keusgen, M. et al., "Characterization of some Allium hybrids by aroma precursors, aroma profiles, and alliinase activity," J. Agric. Food Chem. 50(10):2884-90 (May 2002).
Nomura, et al., "S-Alkylcysteinase: Enzymatic Cleavage of S-Methyl-l-cysteine and Its Sulfoxide," J. Biol. Chem. 238 (4):1441-1446 (Apr. 1963).
Nishimura, H., et al., "Stereoselective synthesis of S-(-prop-1-enyl)-cysteine sulphoxide," Tetra. Lett. 16(37):3201-3202 (Jul. 1975).
Ho, M. F., and Mazelis, M., "The C-S lyases of higher plants, determination of homology by immunological procedures," Phytochemistry 34(3):625-629 (Oct. 1993).
Granger, D.L., Taintor R.R., Boockvar K.S., Hibbs J.B. Jr. "Measurement of nitrate and nitrite in biological samples using nitrate reductase and Griess reaction," Methods Enzymol. 268:142-51 (1996).
Carson, J. F., and Boggs, L. E., "The Synthesis and Base-Catalyzed Cyclization of (+)—and (-)-cis-S-(1-propenyl)-L-cysteine Sulfoxides," J. Org. Chem. 31(9):2862-2864 (Sep. 1966).
Mirelman et al., "Comparison of Use of Enzyme-Linked Immunosorbent Assay-Based Kits and PCR Amplification of rRNA Genes for Simultaneous Detection of Entamoeba histolytica and E. dispar," J. Clin. Microbiol. 35(9):2405-2407 (Sep. 1997).
Prochaska, et al., "Rapid detection of inducers of enzymes that protect against carcinogens," Proc. Natl. Acad. Sci. USA 89:2394-2398 (Mar. 1992).
Eady, C.C., et al., "Silencing Onion Lachrymatory Factor Synthase Causes a Significant Change in the Sulfur Secondary Metabolite Profile," Plant Physiology 147:2096-2106 (2008).
Jones, M.G., et al., "Biosynthesis of the flavour precursors of onion and garlic," J. Exp. Bot. 55 (404):1903-1918 (Aug. 2004).
Kiddle, G.A., et al., "C-S lyase activities in leaves of crucifers and non-crucifers, and the characterization of three classes of C-S lyase activities from oilseed rape (Brassica napus L.)," Plant, Cell and Environment 22:433-445 (1999).
Freeman, G.G. and Whenham, R.J., "The use of synthetic (+/-31)S-1-propyl-L-cysteine sulphoxide and of alliinase preparation in studies of flavour changes resulting from processing of onion (Allium cepa L.)," J. Sci. Food Agric. 26:1333-1346 (Sep. 1975).

* cited by examiner

*Primary Examiner* — Chris R Tate
*Assistant Examiner* — Douglas F White
(74) *Attorney, Agent, or Firm* — Armstrong Teasdale LLP

(57) ABSTRACT

Processes using *Allium* tissue homogenates and extracts in a simple and cost-effective manner to maximize the yields and recovery of thiosulfinates from *Allium* tissues and related organisms possessing alliinase, LF synthase and/or S-alk(en)yl-L-cysteine sulfoxides are disclosed.

13 Claims, 23 Drawing Sheets

US 8,481,284 B2

PROCESS OF PREPARING CONJUGATES OF ALLIUM ORGANOSULFUR COMPOUNDS WITH AMINO ACIDS, PEPTIDES, AND PROTEINS

CROSS REFERENCE TO RELATED APPLICATION

This application claims priority to and benefit of U.S. patent application Ser. No. 61/249,315 filed Oct. 7, 2009, which is hereby incorporated herein by reference in its entirety.

STATEMENT REGARDING FEDERALLY SPONSORED RESEARCH OR DEVELOPMENT

This invention was made with government support under Grant Award Nos. 2005-35503-16328; 97-36200-5189; and 11CRHF-0-6055 awarded by the United States Department of Agriculture (USDA) and Cooperative State Research, Education, and Extension Service (CSREES). The government may have certain rights in the invention.

BACKGROUND OF THE DISCLOSURE

The present disclosure relates generally to processes for the stabilization of organosulfur equivalents derived from *Allium* tissues in a form that retains biological activities relevant to human health promotion. More particularly, *Allium* tissues are specifically combined and reacted to yield thiosulfinate preparations for further utilization in the preparation of mixed disulfide conjugates with thiol-containing residues.

Epidemiological studies having consistently shown that the consumption of *Allium* vegetables (such as onions, garlic, chives, leeks, and the like) have been associated with reduced incidence of many diseases among human populations (Kendler, 1987; Steinmetz and Potter, 1996; Ernst, 1997; Bianchini and Vainio, 2001; Tapiero et al, 2004). The health benefits of *Allium* vegetables are widely attributed to or correlated with the enzyme-transformed organosulfur compounds called thiosulfinates (i.e., fresh-like *Allium* flavors), sulfides (cooked-type *Allium* flavors) and related species.

Specifically, it has been found that thiosulfinates have biological activities related to health-benefits of cancer chemoprotection, anti-inflammatory, antioxidant, and antimicrobial effects, and cardiovascular benefits of cholesterol-, lipid-, and platelet activity-lowering effects, among others (Lawson, 1998; Tapiero et al., 2004). For example, various studies have shown that the administration of fresh garlic, etheric extracts, or its active component allicin (thio-2-propene-1-sulfinic acid) resulted in beneficial effects on cardiovascular risk factors, mainly hyperlipidemia and thrombogenesis in humans. Furthermore, garlic was shown to increase fibrinolytic activity, inhibit platelet aggregation, and reduce serum cholesterol levels. Additionally, garlic juice was shown to inhibit the growth of bacteria of the genera *Staphylococcus, Streptococcus, Vibrio* and *Bacillus*, and of zoopathogenic fungi and many strains of yeast, including *Candida albicans*.

Thiosulfinates in the diet are virtually 100% absorbed by the human body (Lawson and Wang, 2005). The details of their metabolic fate, however, are not known other than that a stoichiometric amount of allyl methyl sulfide is formed from allicin, which provides the basis for determining bioavailability. Furthermore, thiosulfinates in these vegetables have limited stability in fresh minced tissues (Block et al., 1992), and chemically evolve into other organosulfur compounds, principally (poly)sulfides, γ- and α-sulfinyl disulfides, vinyl dithiins, as well as other lesser abundant derivatives, some of which also have limited stability. These subsequent chemical transformations may be evoked by elevated temperature, pH adjustment and the addition of organic solvents to tissue macerates and/or extracts (Block, 1992). In the particular case of bulb onion (*A. cepa*) and related species rich in S-1-propenyl-L-cysteine sulfoxides (1-PeCSO), much of the alliinase-transformation products of 1-PeCSO is lost as propanethial-5-oxide (PTSO) from tissue due to volatility (see FIG. 1); thus this type of instability also leads to a lack of retention of organosulfur equivalents within the tissue matrix and hence, a likely depletion of any health benefits associated with onion consumption. Since PTSO is also the pungent component in freshly cut onions that induces tearing, the presence of PTSO (also called the lachrymatory factor or "LF") is a major reason why some people find fresh-cut raw onions objectionable.

Because of the limited stability of many *Allium* organosulfur components, and uncertainly about which are the most health-relevant agents in intact or processed *Allium* vegetable tissues, efforts have been made to manage the biochemistry of organosulfur evolution in *Allium* vegetable products, both for use as foods and dietary supplements. One approach has been to prepare an immobilized alliinase to react with synthesized S-allyl-L-cysteine sulfoxide (2-PeCSO) to generate the major garlic thiosulfinate, allicin (Mirelman et al., 1997; Miron et al., 2006). The disadvantages of this approach, however, include use of synthetic substrate (2-PeCSO), and the expense of moderately sophisticated technology, concern about long-term stability of the immobilized enzyme, and projected scaling-up of allicin synthesis.

Another approach has made use of aged garlic preparations, where sliced cloves are extracted by prolonged incubation in aqueous ~20% ethanol (Lawson, 1998). The principal organosulfur components that evolve are the S-alk(en)yl-L-cysteine (CySR) and S-alk(en)yl-L-mercaptocysteine (CySSR) species, at a mass ratio of about 5:1, where R is predominantly the allyl group. The resulting product is an aged garlic extract (Kyolic®), marketed as a dietary supplement. Although this product is prepared by rather simple steps, the reported time required for aging is greater than 10 months (Lawson, 1998) (20 months stated on Wakunaga/Kyolic® website accessed 2 Sep. 2009), and the CySR and CySSR organosulfur chemotypes have not been studied for potential health benefits as much as the thiosulfinates and (poly)sulfides; thus, the impact that aged garlic extract may have on disease risk reduction and which components are responsible is not well established by comparison.

Additional approaches including conventional breeding and other molecular biology strategies have also been used to manage the evolution, fate and profile of organosulfur components in *Allium* tissues.

Accordingly, there is a need in the art for developing the means to manage and control the transformation of thiosulfinates and related organosulfur species into stabilized, naturally occurring derivatives retaining biological activity relevant to human health promotion. Additionally, it would be advantageous if the organosulfur equivalents (also referred to herein as mixed disulfide conjugates) could be prepared in a short period of time using simple means.

BRIEF DESCRIPTION OF THE DISCLOSURE

Accordingly, the present disclosure is generally directed to specific processing methods using *Allium* tissue homogenates and extracts in a simple and cost-effective manner to maximize the yields and recovery of thiosulfinates from

*Allium* tissues and related organisms possessing alliinase, LF synthase and/or S-alk(en)yl-L-cy steine sulfoxides. More particularly, in one embodiment, the present disclosure is directed to an in situ enzymatic method to prepare gram-scale pure thiosulfinates, and natural mixtures of thiosulfinates (RS (O)SR(R=methyl, ethyl, propyl, 1-propenyl and allyl) and related species in FIGS. 1 and 2) using an *Allium* tissue homogenate as an alliinase-bearing source. In another embodiment, a process for preparing (multi)gram-scale 1-propenyl-containing thiosulfinates using a blend of an alliinase-bearing tissue homogenate of specific *Allium* species with an LF synthase/alliinase-inactivated onion (or onion-related) tissue (FIG. 2) is disclosed. The thiosulfinates evolved in these processes can be used to prepare mixed disulfide conjugates with cysteine (CYS) and glutathione (GSH), conjugates with proteins, protein hydrolysates, and peptides, and other chemical components bearing thiol groups (R—SH).

Accordingly, in one embodiment, the present disclosure is directed to a process for preparing mixed disulfide conjugates from *Allium* organosulfur compounds. The process comprises: homogenizing an alliinase-bearing tissue source; contacting the homogenate with a source of S-alk(en)yl-L-cysteine sulfoxides (ASCO) to produce a mixture of thiosulfinates; and reacting the mixture of thiosulfinates with a thiol component to produce the mixed disulfide conjugates.

In some embodiments, the process further comprises introducing the homogenate into a solvent to allow for extraction of nascent thiosulfinates that form in the homogenate. Suitable solvents may include hexane, ethyl acetate, ether, methylene chloride, vegetable oils, olive oils, other edible oils, and the like, and combinations thereof.

In some embodiments, the process may further include heating the source of ACSO prior to being contacted with the homogenate. This heating step may allow for the inactivation of any endogenous lachrymatory factor synthase (LF synthase) activity.

In another embodiment, the present disclosure is directed to a mixed disulfide conjugate prepared using the processes described herein. The conjugate comprises a thiosulfinate conjugated to a thiol component. These conjugates show an increased phase 2 enzyme-inducing activity and/or an increased anti-inflammatory effect in cells. As used herein, "phase 2 enzyme" refers to enzymes coordinately regulated by the antioxidant response element, and provides cellular defense to xenobiotics, (pro)carcinogens and oxidative stress. Examples of phase 2 enzymes include quinone reductase, glutathione-5-transferase, and hemeoxygenase-1. Since chronic inflammation is a risk factor of many diseases and pathologies, the identification of dietary or therapeutic agents to suppress inflammation has potential to reduce disease risk.

In yet another embodiment, the present disclosure is directed to a food product comprising one or more of the mixed disulfide conjugates. Exemplary food products may include solid food products such as skim milk and egg whites, proteinaceous food ingredients, or may include liquid beverages such as fruit juices and sports/nutritional beverages.

In another embodiment, the present disclosure is directed to the preparation of mixed disulfide conjugates between thiosulfinates and thiol components of proteins, protein hydrolysates, and peptides. In one aspect, the protein is a native protein. In another aspect, the protein is chemically and/or physically modified. Exemplary proteins may include whey protein isolate, soy protein isolate, crude egg white protein, and keratin.

In still another embodiment, the present disclosure is directed to a food product comprising one or more protein-mixed disulfide conjugates, protein hydrolysate-mixed disulfide conjugates, and peptide-mixed disulfide conjugates. Exemplary food products may include solid food products such as skim milk and egg whites, proteinaceous food ingredients, or may include liquid beverages such as fruit juices and sports/nutritional beverages.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
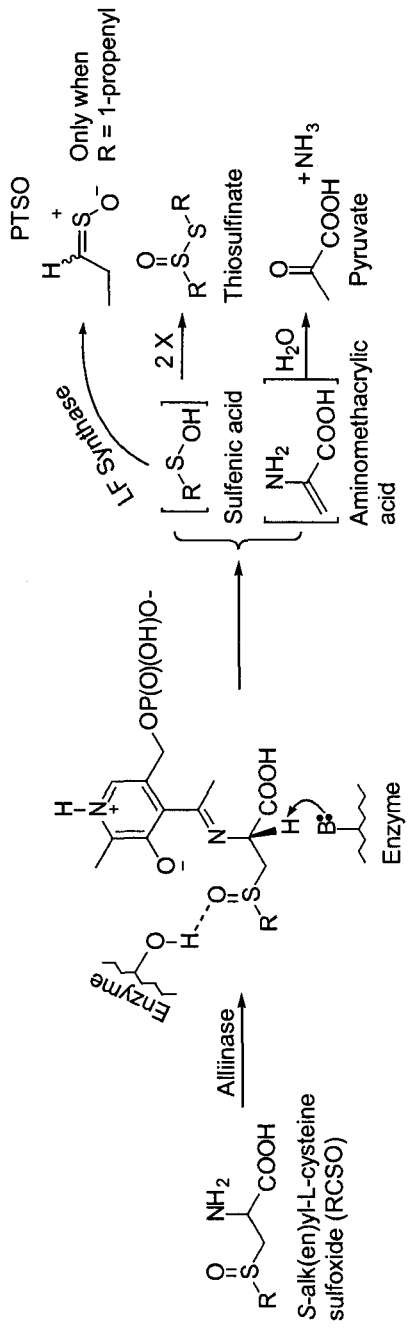
FIG. 1 depicts the reaction mechanisms of alliinase with S-alk(en)yl-L-cysteine sulfoxides (ACSO) to form thiosulfinates and propanethial S-oxide (PTSO).

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF PREFERRED EMBODIMENTS

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the term "thiosulfinates" will be used to collectively refer to thiosulfinates and related organosulfur species, such as PTSO, di-propenyl thiosulfinate rearrangement products, and sulfinyl disulfides, that can evolve and/or accumulate in freshly disrupted *Allium* tissues and extracts where alliinase and ACSO are present.

The present disclosure is generally directed to processes of blending and processing of common *Allium* vegetable tissues to prepare both pure and complex mixtures of thiosulfinates as well as the corresponding mixed disulfide conjugates representative of the full profile of thiosulfinates that exist naturally in *Allium* vegetables and chemotaxonomically-related organisms. In some applications, it is preferred that the alliinase-bearing source is "washed" or solvent-extracted after homogenization as a means to control the final profile of thiosulfinates and related organosulfur species that accumulate. It has been found that these processes produce mixed disulfide conjugates having the biological activity associated with thiosulfinates, especially for the unsaturated thiosulfinate species, that can be retained. More particularly, it has been shown that the prepared mixed disulfide conjugates have a stabilized form of this biological activity relative to the parent thiosulfinates.

The basic steps in the process of the present disclosure include: 1) preparation of an *Allium* tissue homogenate containing active alliinase, 2) sometimes extracting a portion of the nascent thiosulfinates from the homogenate after a predetermined incubation period by a suitable solvent, 3) addition of a secondary, often principal source of ACSO, preferably using an LF synthase/alliinase-inactivated *Allium* tissue source to evolve the final mixture of thiosulfinates, and 4) reacting the thiosulfinates with a thiol component to yield the mixed disulfide conjugates. In some cases a purification step to obtain the final mixed disulfide conjugate preparation may be desired, especially for the purpose of unequivocal assessment of biological activity. The process can be used to prepare thiosulfinates pure in a specific alk(en)yl group from a single ACSO, whether it is synthetic or isolated from a natural source.

Initially, an *Allium* tissue homogenate is prepared. Typically, the tissue homogenate is prepared by homogenizing an alliinase-bearing tissue source at ambient (room) temperature within the range of from about 0° C. to about 40° C., as long as tissue enzymes are not denatured. Tissue homogenates prepared at about 4° C. to about 20° C. are most conducive for retention of enzyme activity, especially when multiple stages of reaction or extractions are planned. Virtually any tissue source of alliinase can be used, although there are kinetic and capacity advantages of processes where the source is among the more abundant in alliinase, such as garlic. Other suitable *Allium* tissue sources of alliinase may include, for example, chives, leeks, onions, and mixtures thereof, and non-Allium sources such as *Tulbaghia violacea, Brassica* spp., including cabbage broccoli, rutabaga, and rapeseed, *Albizzia lophanta, Penicillium corymbiferum, Pseudomonas* spp., *Bacillus subtilis, Acacia farnesiana*, Shitake mushroom, and spinach (Nomura, 1963; Schwimmer, 1986; Ho and Mazelis, 1993; Kiddle et al., 1999). Recombinant alliinase expressed in other organisms would also be suitable.

An important feature of the alliinase-bearing tissue source(s) is that it does not contain "LF synthase" activity, or if it does, then the principal ACSO source should preferably not contain 1-PeCSO. LF synthase is a recently identified enzyme activity in onion that is responsible for causing the transformation/isomerization of the 1-propenyl sulfenic acid (1-PeSOH) to the propanethial S-oxide (PTSO) (Imai et al., 2002; Eady et al., 2008), the latter which is also referred to as the lachrymatory factor (LF). Because of its only recent discovery, LF synthase activity has not yet been classified as an enzyme by the International Union of Biochemistry and Molecular Biology Nomenclature Committee. Presently, it is not known whether the synthase is an enzyme completely distinct from alliinase, or if it is an alliinase isoform that also facilitates the isomerization process. Alternatively, it is possible the LF synthase is a non-catalytic protein that facilitates the isomeriziation of 1-PeSOH to PTSO, similar in function to the epithiospecifier proteins found in many species of the Brassicaceae family that cause isomerization of intermediates of glucosinolate transformation initiated by myrosinase (Wittstock and Burow, 2007). Regardless, it is easy to determine if a preparation sourced from any species of *Allium* or chemotaxomically-related organism possesses LF synthase activity by determining that PTSO/LF is formed from any substrate comprised in part or in whole of S-1-propenyl-L-cysteine sulfoxide (1-PeCSO). Some studies have surveyed commercially important species of the *Allium* Genus for the ability of macerated tissues to form PTSO (Block et al, 1992), which is easily lost to volatility. This feature is most relevant for processes intended to yield preparations of thiosulfinates that retain 1-propenyl functional groups to use "as is" or to prepare mixed disulfide conjugates with thiol reagents from these thiosulfinate-rich preparations. If no 1-propenyl containing ACSO substrates or thiosulfinates are to be involved in the process, then it is not as important whether the alliinase-bearing tissue source possesses LF synthase activity.

For a typical preparation, an *Allium* tissue is homogenized with an aqueous solution using a mechanical blender or comminuting device at ambient (room) temperature within the range of from about 0° C. to about 40° C. A minimum amount of aqueous solution (or buffer) is preferred for the homogenization step as this maximizes alliinase concentration in the homogenate. The homogenate is then incubated at ambient (room) temperature for up to 2 hours, and preferably for approximately 40 to 60 minutes and filtered. The homogenate is then ready for use for further enzymatic generation of thiosulfinates from an added source of ACSO.

Once homogenized, the *Allium* tissue blends contain health-promoting components, rich in thiosulfinates. These homogenates can be used directly as a food ingredient or food product themselves.

As an alternative, alliinase-bearing tissue sources can be used as dried tissue powders (that have not been subject to sufficient heat to inactivate alliinase), or crude or partially purified protein extracts. The latter preparations are often used as initial steps in enzyme purification (such as in Thomas and Parkin, 1991, for alliinase). The rationale for using these types of alliinase preparations is to be able to increase concentrations of alliinase in the reconstituted reaction systems with ACSO, affording kinetic and capacity advantages for the intended process.

An optional step prior to combining the alliinase-bearing source with added ACSO source is to extract the alliinase-bearing homogenate or filtrate with an equal amount of ethyl acetate (EtOAc) or other organic solvent (phase separation process can be hastened by centrifugation or sonication). Upon tissue disruption, transformation of ACSO substrate by the alliinase leads to progressive accumulation of thiosulfinates in the host tissue. Extracting or "washing" the homogenate with a water-immiscible organic solvent, such as hexane, ethyl acetate, ether, methylene chloride, among others, including vegetable oil and olive oil, will deplete the homogenate of a large proportion of the nascent thiosulfinates that form in the homogenate.

Figure 3:
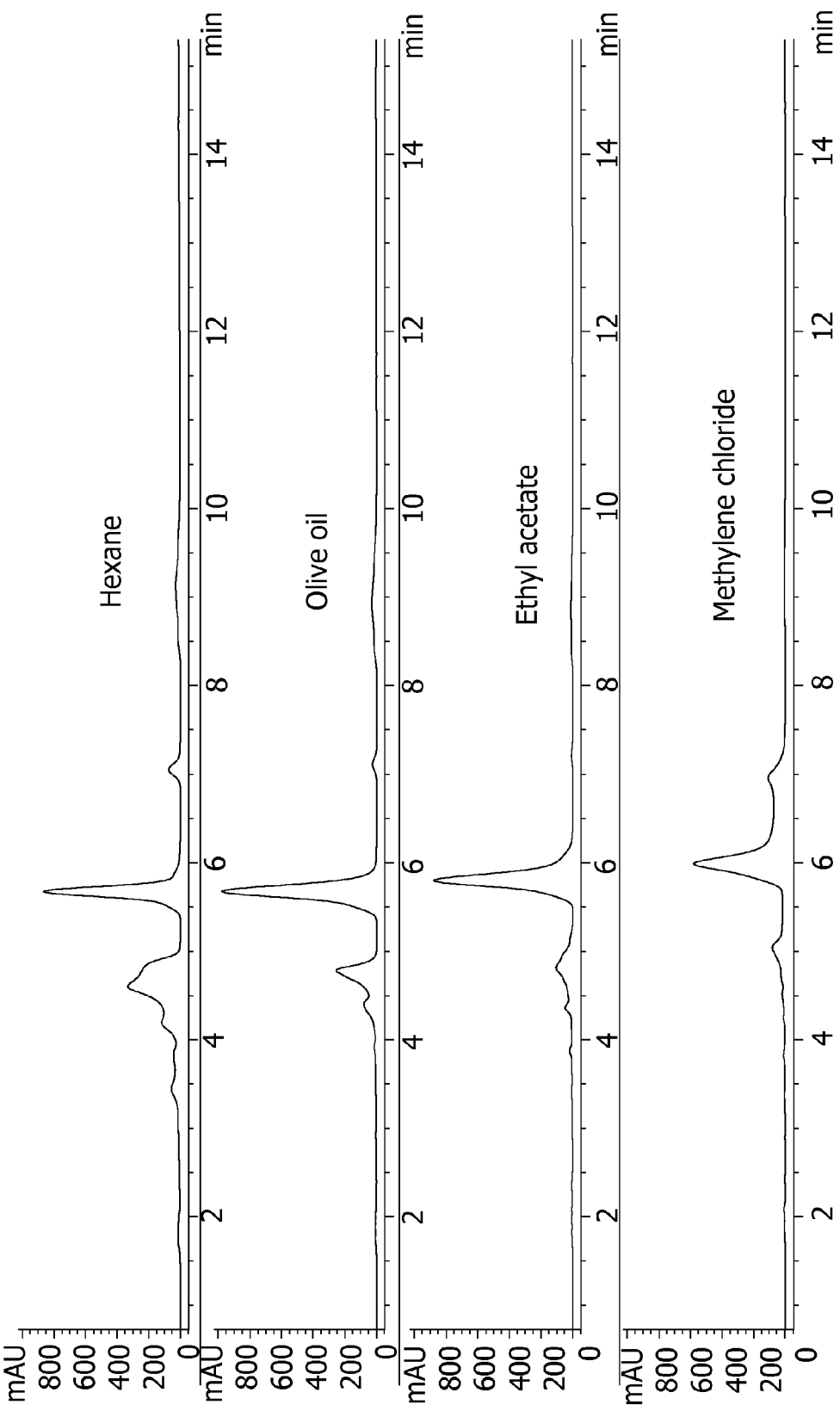
FIG. 3 depicts the extraction of garlic homogenate with various solvents, followed by the addition of (±)-S-ethyl-L-cysteine sulfoxide (ECSO).

The homogenate may be extracted or washed in the solvent at ambient (room) temperature for a period sufficient to remove the nascent thiosulfinates that form in the homogenate, such as for a time period of from about 5 minutes to about 5 hours. HPLC may be used to monitor the profile of extracted thiosulfinates (FIG. 3). Components eluting in the 4-5 minute retention time window are residual garlic thiosulfinates, and the peak at 6 minutes is the diethyl thiosulfinate. It has been found that methylene chloride ($CH_2Cl_2$) and ethyl acetate (EtOAc) are the most effective at extracting thiosulfinates (lower levels of garlic thiosulfinates retain in the washed homogenate) (see FIG. 3). However, extraction with $CH_2Cl_2$ resulted in lower subsequent conversion of ECSO to diethyl thiosulfinate (smaller peak at 6 minutes), indicating that some alliinase deactivation occurred. The hexane and olive oil was less capable of extracting residual thiosulfinates, but had little deactivating effect on alliinase in the homogenate. Thus, EtOAc is a particularly preferred solvent.

Other preferred solvents include water-immiscible non-polar solvents with a log P(P=partitioning coefficient between 1-octanol:water) of approximately 0.7-2.0, that matches the range of log P values for thiosulfinates. Low-boiling solvents that meet these criteria are also preferred as they facilitate recovery of extracted thiosulfinates for useful purposes, especially if the solvent is to be removed to afford neat thiosulfinate preparations.

The proportion of nascent thiosulfinates removed will depend on the amount of time elapsed between homogenization and extraction with solvent. For example, extracting with solvent soon after homogenization will deplete the host tissue of most of the thiosulfinates that evolve to that point. Electing not to extract nascent thiosulfinates (i.e., no washing step) will serve to retain those thiosulfinate equivalents in the mixture when any additional source(s) of ACSO is infused and allowed to react with the alliinase. After extraction, the alliinase will continue to transform any residual ACSO in the original "washed" homogenate, in addition to any further ACSO infused from synthetic or natural *Allium* or other tissue source(s). After prolonged incubation of the alliinase-bearing tissue homogenate, whereupon reaction on intrinsic ACSO is essentially exhausted, solvent extraction will remove nearly all of the thiosulfinates that can evolve in that tissue homogenate. The election and timing of the post-homogenization extraction or washing affords a simple measure of control over the ultimate profile of thiosulfinates that evolves in tissue blends, which may depend on the intended use of the thiosulfinates. The washing or extraction step may also remove reaction products that may inhibit the alliinase in the tissue (Schwimmer et al., 1964; Miron et al., 2006). This washed tissue extract can then be used for further enzymatic generation of thiosulfinates from an added source of ACSO.

Figure 2:
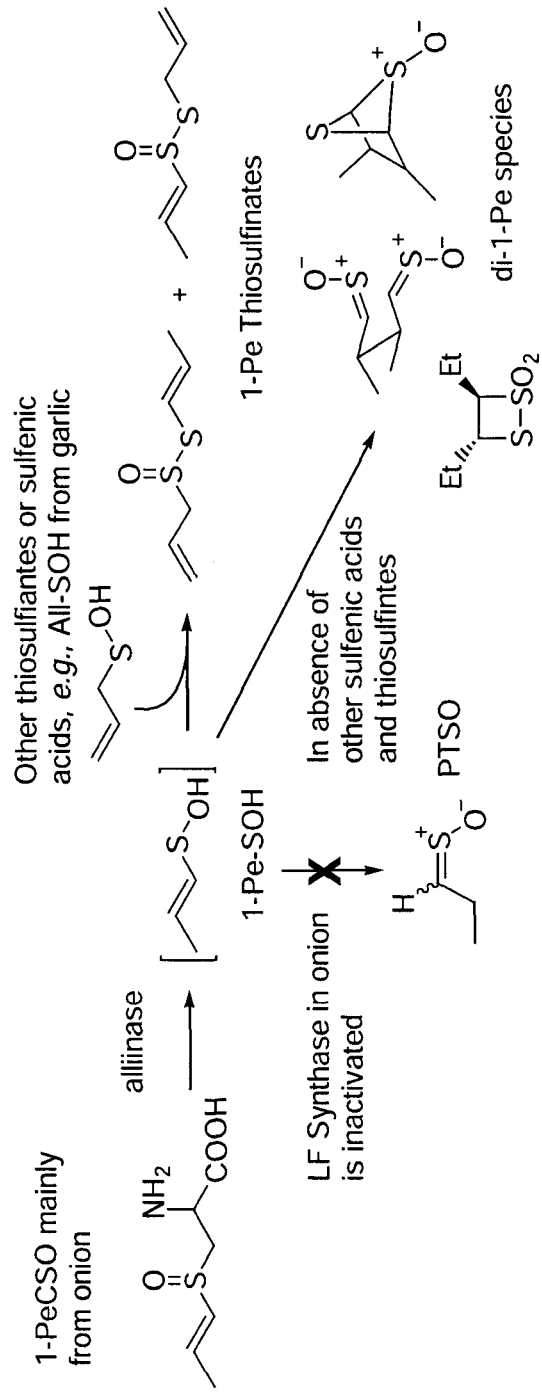
FIG. 2 depicts the reaction mechanisms and fate of organosulfur components as influenced by inactivating lachrymatory factor synthase (LF synthase) in onions.

A particularly important application of this "washing" step is to deplete an alliinase-bearing tissue homogenate of most of the nascent thiosulfinates that normally evolve. For example, the combination of the "washed tissue homogenate" with alliinase-inactivated onion tissue will allow onion di-1-propenyl and mixed thiosulfinates to accumulate while minimizing LF/PTSO evolution. Some residual thiosulfinates originating in the "washed tissue homogenate" can be useful to promote the formation of mixed thiosulfinates containing 1-propenyl residues (FIG. 2). The depletion of nascent thiosulfinates in a more exhaustively washed tissue homogenate of the alliinase-bearing source favors the formation of di-1-propenyl thiosulfinate species that may further evolve to more exotic and difficult to prepare derivatives: bis-sulfines, dithiatane dioxides and "zweibelanes". Such derivatives are preferred end-products of reaction of alliinase in the washed tissue homogenate with 1-PeCSO contributed by the secondary tissue source in reactive mixtures void in LF synthase.

Once prepared, the "washed" or "unwashed" homogenate is contacted with a source of S-alk(en)yl-L-cysteine sulfoxide substrate (ACSO) to produce a mixture of thiosulfinates. One type of ACSO source can be chemically synthesized components (Lancaster and Kelly, 1983; Shen and Parkin, 2000), used in pure form or simple mixtures. Synthetic ACSO sources that reflect naturally occurring ACSO include: ($\pm$)-S-Methyl-L-cysteine sulfoxide (MCSO), ($\pm$)-S-ethyl-L-cysteine sulfoxide (ECSO), ($\pm$)-S-propyl-L-cysteine sulfoxide (PCSO), ($\pm$)-S-1-propenyl-L-cysteine sulfoxide (1-PeCSO), and ($\pm$)-S-2-propenyl-L-cysteine sulfoxide (2-PeCSO) shown in Table 1.

TABLE 1

Synthetic ACSO Sources.

| | |
|---|---|
| MCSO | [structure: methyl sulfoxide cysteine] |
| ECSO | [structure: ethyl sulfoxide cysteine] |
| PCSO | [structure: propyl sulfoxide cysteine] |

TABLE 1-continued

Synthetic ACSO Sources.

| | |
|---|---|
| 2-PeCSO | (structure: allyl-S(=O)-CH2-CH(NH2)-COOH) |
| 1-PeCSO | (structure: propenyl-S(=O)-CH2-CH(NH2)-COOH) |

The S-1-propenyl-L-cysteine sulfoxide (1-PeCSO) is difficult to synthesize (Carson and Boggs, 1966; Nishimura et al., 1975) and is best obtained from natural sources (onion is the most abundant source). Synthetic ACSO sources are useful for preparing pure homologous thiosulfinates or defined mixtures, but reaction with alliinase is slowed because synthetic sources are (±)diastereomeric and alliinases are selective for the naturally occurring (+) diastereomer over the (−) diastereomer.

Alternatively, peptide- and amino acid-rich isolates containing ACSO can be isolated from natural sources and tissues by well known and established techniques. These approaches involve homogenizing or extracting tissues in aqueous acid media, sufficient water miscible alcohols to bring alcohol level to typically ~80% (20% aqueous), or solvent mixtures (e.g., methanol:chloroform:water system) followed by phase separation to yield a de-proteinized low molecular weight isolate from the host source. In one embodiment, the tissue is extracted using an extraction temperature of from about 4° C. to about 40° C. Further enrichment of ACSO from these amino acid and peptide isolates is facilitated by common methods of size exclusion or ion exchange chromatography.

Natural (tissue) sources of ACSO may also be used. As noted above, it is preferable to inactivate any endogenous LF synthase activity in these sources prior to use, especially if the ACSO source contains substantial proportion of 1-PeCSO. Enzyme inactivation is accomplished by the use of any means commonly used to inactivate enzymes including, but not limited to: heating, microwaving, pH adjustment or treatment with any chemical inhibitors/inactivators of alliinase/LF synthase. For example, in some embodiments, the ACSO tissue source is heated to a temperature of from ambient temperature to about 95-100° C. for a time period of from about 2 to about 4 minutes. Other combinations of times and temperatures (for example at 60° C. for 30 minutes, and progressively lower times at higher temperatures) are suitable for deactivating alliinase/LF synthases depending on the thermal sensitivity of the enzyme from various sources. In addition, the processes of hot-air drying, pickling and freezing can be used to cause enzyme inactivation. In another embodiment, the pH of the ACSO source is adjusted to less than 2 and greater than 9, as it has been found that adjustment of the pH of the source to less than 2 and greater than 9 is sufficient to deactivate residual alliinase/LF synthase activity. It should be noted that it is not always necessary to inactivate alliinase in the secondary ACSO-bearing tissue sources. Examples of when additional alliinase from the ACSO-bearing tissue source are productive to the process include, but are not limited to, 1) to supplement alliinase activity in the mixture to provide process rate enhancement or compensate for decay of alliinase derived from the alliinase-bearing tissue source and 2) when the supplemental source of alliinase provides reaction selectivity that is favorable to forming the desired thiosulfinates for the process.

Whatever method is selected for the purpose of inactivating alliinase/LF synthase in the principle ACSO source, it is essential to reach conditions where the enzyme activity contributed by the alliinase-bearing tissue source is preserved upon blending of the washed tissue homogenate and the alliinase-inactivated supplemental ACSO source. For example, a chemical alliinase-deactivating agent would be difficult to employ in the supplemental tissue ACSO source since it could be carried over and risk inactivating enzyme activity in the alliinase-bearing source upon blending of the two preparations.

Upon blending the two preparations, a mixture of thiosulfinates are formed. Typically, the thiosulfinates have the general formula:

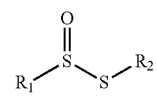

wherein $R_1$ and $R_2$ are independently selected from the group consisting of alkyl, alkenyl, and mixtures thereof. More specifically, the thiosulfinates have structures selected from the formulas:

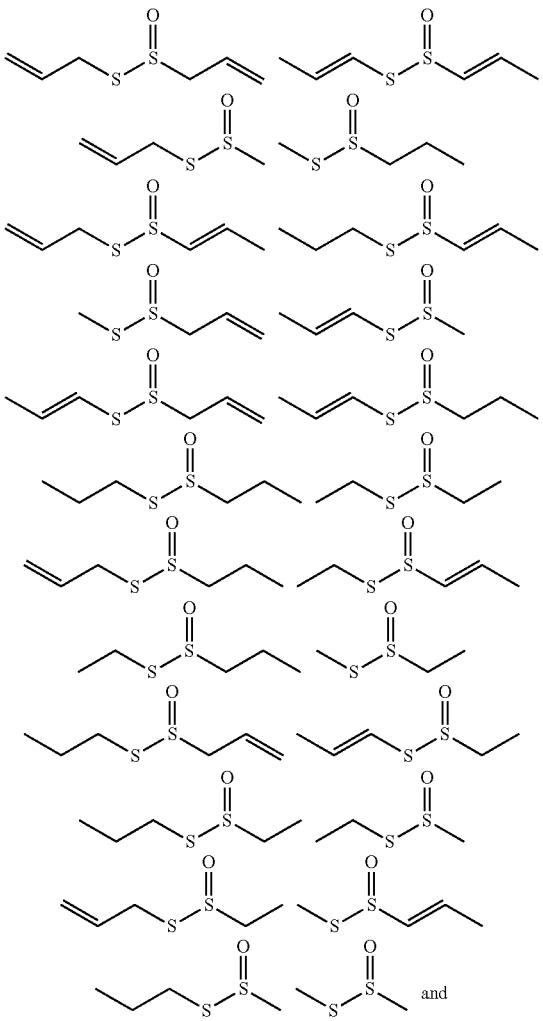

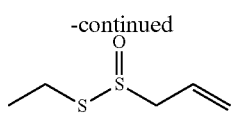

In some embodiments the mixed thiosulfinates may be purified using any methods known in the art prior to any further processing. For example, the thiosulfinates may be purified using filtering, centrifugation, solvent partitioning, chromatography on normal and reverse phase, ionic exchange media, and the like.

After the thiosulfinates have been prepared, the mixture of thiosulfinates is reacted with a thiol component to produce the mixed disulfide conjugates. Generally, the thiol component can be any component known in the art bearing thiol groups (R—SH) or that can be generated by reducing disulfide residues (—SS-→2x-SH). Particularly preferred thiol components include cysteine and glutathione.

In another embodiment, the thiol component may be derived from a protein, protein hydrolysate, and a peptide. The process includes homogenizing an alliinase-bearing tissue source. The homogenate is then contacted with a source of S-alk(en)yl-L-cysteine sulfoxides (ACSO) to produce a mixture of thiosulfinates. The thiosulfinates are then reacted with a thiol component from a protein, protein hydrolysate, or a peptide to produce the mixed disulfide conjugates.

Proteins may be obtained by any method known in the art. Suitable methods may be, for example, by extraction, isolation and purification, recombinant protein expression, and/or commercially available sources.

In one aspect, the protein is a native soluble protein. In another aspect, the protein is a modified protein. Proteins may be modified to enhance the reactivity of protein cysteine groups. As used herein, "modified protein" refers to a protein that is treated in a manner sufficient to unfold the protein to expose cysteine residues, break disulfide bonds, generate free cysteine (—SH) from —SS-residues, and combinations thereof. Suitable methods for modifying proteins are known by one skilled in the art. For example, proteins may be modified by elevating the temperature, combining the proteins with emulsifiers/surfactants, reacting the proteins with compounds to break disulfide bonds, and combinations thereof. Suitable chemical treatments may be, for example, treatment with emulsifiers/surfactants, such as sodium dodecyl sulfate (SDS), diacetyltartaric acid esters of monoacylglycerols (DATEM) and polyoxyethylene sorbitan esters (commonly referred to as polysorbates or TWEENS), and/or treatment with disulfide bond cleavage or reducing agents, such as sodium borohydride, sodium bisulfate, β-mercaptoethanol, dithiothreitol, sodium sulfide, trialkyl phosphines (e.g., tris (2-carboxyethyl)phosphine) and alkaline conditions.

Protein preparations may also include optional dialysis steps prior to conjugation reactions to remove non-protein material and/or —SH reactive material, which may interfere with conjugation reactions. In addition, removal of —SH reactive material in thiosulfinate preparations may be achieved by derivatization with iodoacetate followed by solvent back-extraction of thiosulfinates to remove excess iodoacetate prior to reaction with proteins. The non-alliinase-bearing (i.e., preheated to deactivate alliinase/LF synthase) tissue ACSO source may be homogenized and extracted with organic solvent to remove —SH reactive material prior to generation of thiosulfinates by combining the solvent-washed homogenate to the alliinase-bearing source. These measures are important for monitoring the progress of conjugation reactions. However, they may not be necessary for the purpose of using the described processes to prepare conjugates for practical use.

In another embodiment, the thiol component is a protein hydrolysate. Suitable enzymes for protein hydrolysis include, for example, pepsin, trypsin, chymosin, chymotrypsin, pancreatin, plant/fruit proteases, such as bromelain, ficin, papain, and other protease-containing preparations that are allowed to be added to comestibles, and combinations thereof. Fruit proteases such as, for example, sulfhydryl proteases are particularly suitable for preparing foods, nutritionals, and beverages. Suitable sulfhydryl proteases may be, for example, bromelain, papain, actinidin. Following hydrolysis, the resulting hydrolysates may be further purified. For example, hydrolysates may be passed through a thiol-capturing medium such as thiopropyl Sepharose, activated with dithiodipyridine and infused with peptides. Peptides-SH species are covalently captured by the column while non-cysteine containing peptides flow through. Captured peptides-SH may be eluted by infusing the column with β-mercaptoethanol to reduce column-S—S-peptide complexes to release thiol-containing peptides. Thiol-containing peptides (e.g., hydrolysates) can then be conjugated with thiosulfinates according to the previously described process.

Proteins, modified proteins, and protein hydrolysates may be solubilized with a solubilizing agent. Suitable solubilizing agents may further be urea, guanidine-HCl, SDS or other emulsifiers, sodium sulfite, acid or alkali, or reducing agents (e.g., sodium borohydride, sodium bisulfate, β-mercaptoethanol, dithiothreitol, sodium sulfide, trialkyl phosphines), or proteolytic enzymes (e.g., pepsin, trypsin, bromelain, ficin, papain, chymosin, chymotrypsin, pancreatin), or combinations of these agents.

Exemplary proteins useful in the process may be whey protein isolate, soy protein isolate, crude egg white protein, purified egg albumin, and keratin. Table 2 summarizes the proportion of cysteine and disulfide residues known for exemplary proteins.

TABLE 2

Comparative potential of proteins to deliver bioactive organosulfur compounds (OSC) as mixed disulfide conjugates (MDC) derived from Alliums.

| | | | Protein | | | |
|---|---|---|---|---|---|---|
| Garlic | Onion | | Egg White | Whey Protein Isolate | Soy Protein Isolate | Keratin |
| ~40 μmol ACSO/gfw | ~20 μmol ACSO/gfw | CySH→ | 48 | 28 | 25 | <36 |
| | | CySSCy→ | 77 | 126 | 26 | >342 |
| | | Total→ (μmol/gdw) | 202 | 282 | 77 | ~720 |
| 5 cloves | 1 onion | daily use per | 5 g | 5 g | 5 g | 5 g |

TABLE 2-continued

Comparative potential of proteins to deliver bioactive organosulfur compounds (OSC) as mixed disulfide conjugates (MDC) derived from Alliums.

| | | | Protein | | | |
|---|---|---|---|---|---|---|
| Garlic | Onion | | Egg White | Whey Protein Isolate | Soy Protein Isolate | Keratin |
| (~3 g) 0.12 as OSC | (~21 g) 0.41 as OSC (much lost) | capita max. delivered (mmol) | prospective 1.0 as MDC | prospective 1.4 as MDC | prospective 0.4 as MDC | prospective 3.6 as MDC |

Daily per capita consumption of Alliums obtained from Agricultural Statistics 2008, www.nass.usda.gov, accessed 1 Apr. 2009

Suitable temperatures for producing the mixed disulfide conjugates via thiosulfinates-protein conjugation reactions may be from about 4° C. to about 100° C., and more suitably from about 5° C. to about 80° C. The higher temperatures in this range may cause aggregation and loss of functionality of proteins, but conjugation reactions between thiosulfinates and protein-SH groups still occur. In fact, greater extent of conjugations occurs for thermally-unfolded protein because of unmasking of protein-SH groups. Suitable pH for conjugation reactions may be from about 3 to about 9. Suitable molar ratios of thiosulfinates to thiol components (e.g., cysteine groups from the protein, protein hydrolysate, or peptide) for conjugation reactions range widely and may be about 1:2 to about 10:1. For small peptides, a thiosulfinate:peptide—SH molar ratio of 1:2 is most efficient; this is because the stoichiometry of this conjugation reaction with —SH groups readily available for reaction is known. Because of secondary and tertiary structure (i.e., conformational folding) of the proteins, some protein-SH groups are readily available for reaction, while other protein-SH groups are buried or masked. The former protein-SH groups will react efficiently at a thiosulfinate:peptide—SH molar ratio of 1:2. The latter protein-SH groups are kinetically slower or recalcitrant to reaction and will require a greater proportion of thiosulfinates, approaching a thiosulfinate:peptide-SH molar ratio of 10:1 or more for reaction to occur. Other protein-SH groups in native proteins will not react with thiosulfinates, and chemical and/or physical perturbations of protein structure are required to make these groups available for reaction by exposing buried protein-SH groups to conjugation with thiosulfinates.

Exemplary mixed disulfide conjugates prepared using the processes of the present disclosure include those having the formulas:

TABLE 3

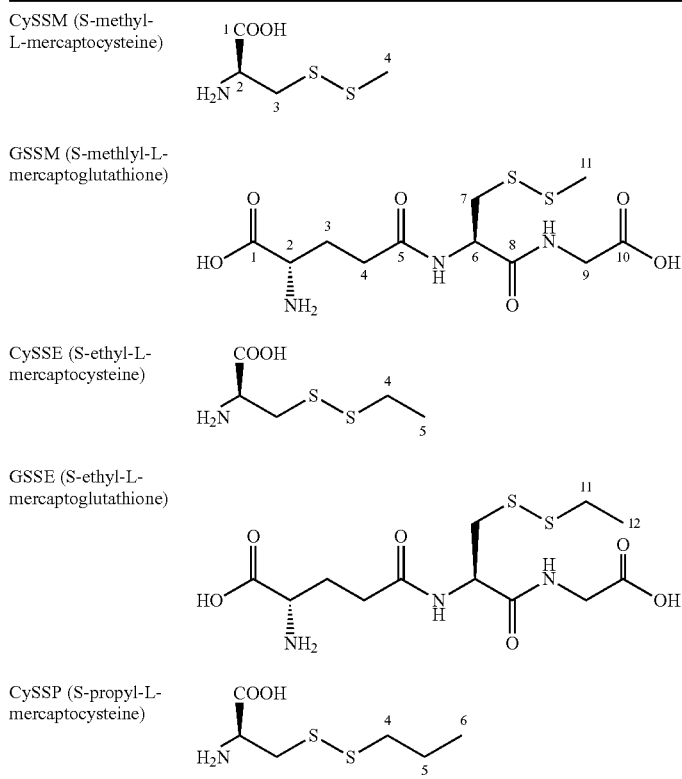

Mixed Disulfide Conjugates.

CySSM (S-methyl-L-mercaptocysteine)

GSSM (S-methlyl-L-mercaptoglutathione)

CySSE (S-ethyl-L-mercaptocysteine)

GSSE (S-ethyl-L-mercaptoglutathione)

CySSP (S-propyl-L-mercaptocysteine)

TABLE 3-continued

Mixed Disulfide Conjugates.

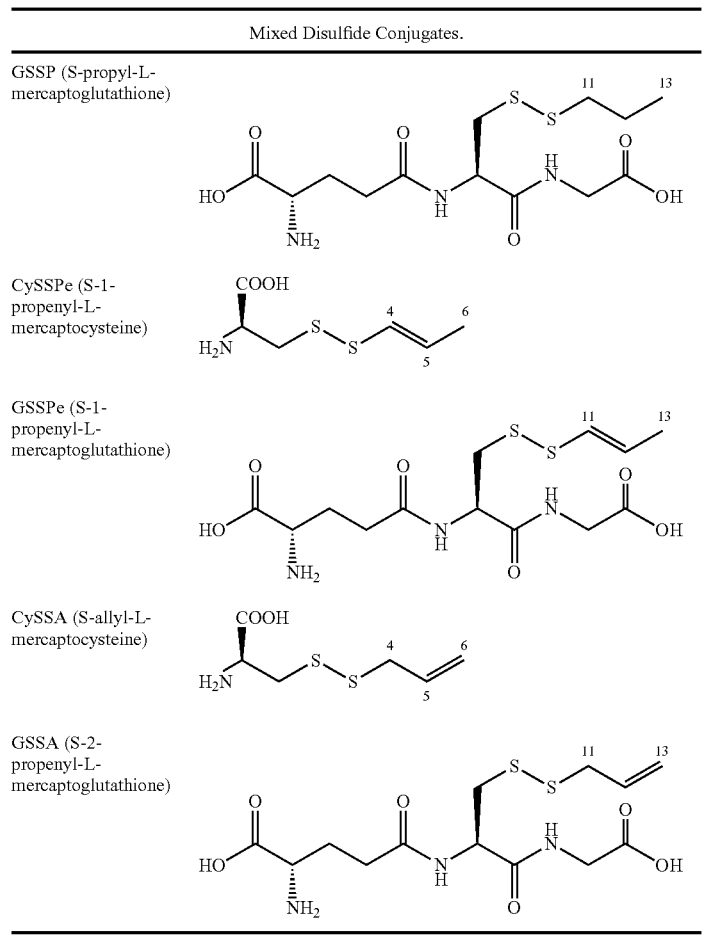

The mixed disulfide conjugates have been shown to have phase 2 enzyme-inducing activity, anti-inflammatory effects, and/or redox and thiol modulating effects in cells, and may be used in food products to provide these health benefits to consumers.

Further, it has been discovered that the mixed disulfide conjugates may be used in food products to reduce cholesterol. Suitable food products for use with the mixed disulfide conjugates may include both solid and liquid food products as known in the art that include proteins and peptide ingredients. For example, the mixed disulfide conjugates may be added to products including whey and soy proteins, such as skim milk or egg whites, to produce a solid food product for consumption. Other exemplary food products including the mixed disulfide conjugates may include, for example, infant formulas, beverages and bars (e.g., sports, herbal, and nutritional beverages), sauces, soups, gravies, dressings, skim milk, egg whites, yogurt, meat products (e.g., vegetarian burgers, sausages), fruit and/or vegetable preparations (e.g., salsa, relishes, etc.), baked goods (e.g., breads, desserts), and the like.

In another embodiment, the mixed disulfide conjugates are mixed with one or more additives containing a protease enzyme and added to food products to digest the foods to produce liquid food products containing the mixed disulfide conjugates. These protease enzymes are involved in a multitude of physiological reactions arising from simple digestion of food proteins to highly-regulated cascades (e.g., the blood-clotting cascade, the complement system, apoptosis pathways, and the invertebrate prophenoloxidase-activating cascade). Exemplary protease enzymes include: serine proteases, threonine proteases, cysteine proteases, aspartate proteases, metalloproteases, and glutamic acid proteases. These enzymes are commonly found in various plants such as in fruit extracts including pineapple, kiwi, or papaya, or animal digestive organisms, or other commercial enzyme preparations containing proteases as allowed to be used in foods. When added with these additives, the mixed disulfide conjugates can be included in liquid products such as fruit juices and nutritional/sport beverages.

The disclosure will be more fully understood upon consideration of the following non-limiting Examples.

EXAMPLE 1

In this Example, an alliinase-bearing tissue source for use in the process of the present disclosure is prepared.

Specifically, about 100 g garlic tissue is homogenized with 20 ml water with a mechanical blender or comminuting device at ambient (room) temperature. The homogenate is then incubated at ambient (room) temperature for 40 to 60 minutes, filtered through cheesecloth, and then extracted with an equal volume of organic solvent. This washed tissue extract has sufficient residual alliinase activity for further enzymatic generation of thiosulfinates from an added source of ACSO.

EXAMPLE 2

In this Example, onion bulbs are immersed in boiling water to inactivate alliinase/LF synthase as described in one embodiment of the processes of the present disclosure.

To begin, onion bulbs are quartered and the fleshy scales are separated in a manner to minimize tissue disruption. In some cases, it may be preferable to coarsely cut or prepare tissue for alliinase/LF synthase inactivation in a manner that maximizes surface area to facilitate heat transfer, while minimizing tissue disruption. Segments are placed in a boiling water bath, preferably at 95-100° C., preferably at a mass-volume ratio of 1:5 (typical range of 1:20 to 1:1) to afford rapid heat transfer and heat penetration into the tissue. After heat treatment for a prescribed period of time of up to 4 minutes, the tissue is cooled, homogenized with 0.5 volume of water (or preferably cooled heating water), allowed to incubate for 40 minutes after which thiosulfinate levels were measured by an N-ethylmaleimide colorimetric reagent (Nakata et al., 1970) as evidence of residual enzyme activity. Results in Table 4 show that heating under these conditions for at least 2 minutes is sufficient to deactivate residual alliinase/LF synthase activity. The residual thiosulfinate levels of <5% are likely derived from thiosulfinates and/or their thermal transformation products generated during the heating period, and sulfhydryl components in tissue that also test positive in this assay.

TABLE 4

Effect of boiling bulb tissue segments in water on residual allinase/LF synthase in onion.

| Boiling time (minutes) | Relative levels (%) of thiosulfinates formed |
|---|---|
| 0 | 100 |
| 1 | 61 |
| 2 | 4 |
| 3 | 4 |
| 4 | 2 |

EXAMPLE 3

In this Example, onion bulbs are heated by microwave energy to inactivate alliinase/LF synthase as described in one embodiment of the processes of the present disclosure.

To begin, an onion bulb as in Example 2 and about 300 g tissue portions were placed in a compact domestic microwave for a prescribed period of time of 0-4 minutes. The tissue was cooled, homogenized with 0.5 volume of water, allowed to incubate for 40 minutes, after which thiosulfinate levels were measured by an N-ethylmaleimide colorimetric reagent as evidence of residual enzyme activity. Results in Table 5 show that heating under these conditions for at least 3 minutes is sufficient to deactivate residual alliinase/LF synthase activity. The residual thiosulfinate levels of ≦6% likely are caused by thiosulfinates and/or their thermal transformation products generated during the heating period, and sulfhydryl components in tissue that also test positive in this assay.

TABLE 5

Effect of microwave heating on residual alliinase/LF synthase activity in onion bulb tissue segments.

| Microwave time | Relative levels (%) of thiosulfinates formed |
|---|---|
| 0 | 100 |
| 1 | 101 |
| 2 | 27 |
| 3 | 6 |
| 4 | 1 |

EXAMPLE 4

In this Example, the pH of an onion tissue was adjusted to inactivate alliinase/LF synthase as described in one embodiment of the present disclosure.

To begin, the tissue was homogenized with preferably 0.5 volumes of aqueous acidic (HCl) or alkaline (NaOH) medium to yield a range of pH conditions in the homogenate. After incubation for 40 minutes, thiosulfinate levels were measured by an N-ethylmaleimide colorimetric reagent as evidence of residual enzyme activity.

Results in Table 6 show that attaining a pH of <2 and >9 in tissue homogenates is sufficient to deactivate residual alliinase/LF synthase activity. The residual thiosulfinate levels of ≦6% are likely caused by thiosulfinates generated early in the homogenization period before homogeneous pH conditions were established, and sulfhydryl components in tissue that also test positive in this assay, both of which are known to be sensitive to decay at alkaline pH (which explains why none were detected at pH>9).

TABLE 6

Effect of pH adjustment on residual alliinase/LF synthase activity in pH-adjusted onion bulb tissue homogenates.

| pH of homogenate | Relative levels (%) of thiosulfinates formed |
|---|---|
| 1.6 | 6 |
| 2.2 | 5 |
| 3.1 | 58 |
| 4.2 | 100 |
| 5.4 | 85 |
| 7.7 | 36 |
| 8.6 | 10 |
| 9.8 | not detected |
| 10.7 | not detected |
| 11.6 | not detected |

EXAMPLE 5

In this Example, the garlic homogenate as prepare in Example 1 was combined with a source of ACSO to produce thiosulfinates.

The garlic homogenate was allowed to incubate for an extended period of time, approximately 60 minutes and then "washed" twice by equal volumes of EtOAc and found to be essentially free of residual thiosulfinates. Then a fixed amount of individual ACSO was dissolved in 10 ml water and added to 90 ml of the washed garlic homogenate. After subsequent incubation for 40-60 minutes, the newly generated thiosulfinates were extracted and analyzed by HPLC (Table 6). Yields were calculated based on the weights of added ACSO and recovered thiosulfinate, and the molar stoichiometry of 2 mol ACSO required to form 1 mol thiosulfinate (FIG.

1). One advantage of this process over the prior art was that almost complete conversion of the (±) diastereomeric ACSO species was approached for 2-PeCSO and >50% for two others (Table 7). Previous efforts have noted the slow, recalcitrant reactivity of alliinase with the (−) ACSO species. The high yields in the instant process are attributed to the high level of alliinase afforded by using tissue homogenates. The relative yields can be explained by the known ACSO selectivity of 1-PeCSO≦2-PeCSO>PCSO≦ECSO>MCSO for crude alliinases (Freeman and Whenham, 1995; Shen and Parkin, 2000; Keusgen et al., 2002).

TABLE 7

The yields of multi-gram scale enzymatic reactions.

| ACSO Species | Weight of ACSO | Weight of Thiosulfinate | Yield (molar basis) |
|---|---|---|---|
| MCSO | 3.26 g | 0.5 g | 42% |
| ECSO | 3.55 g | 1.0 g | 67% |
| PCSO | 2.00 g | 0.6 g | 65% |
| 2-PeCSO | 4.00 g | 2.0 g | 99% |

Figure 4:
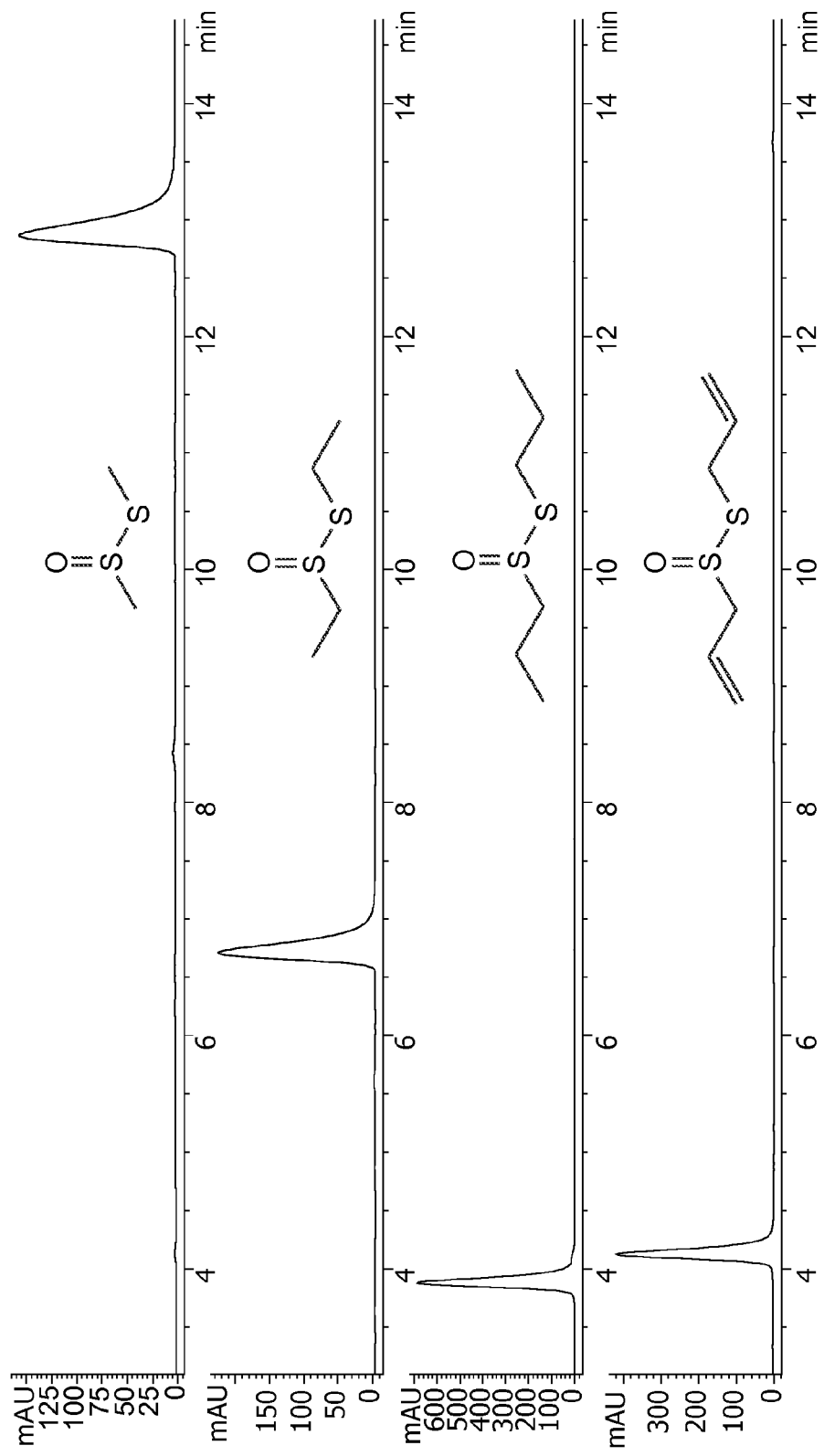
FIG. 4 depicts the HPLC analysis of thiosulfinates as prepared in Example 5.

This example shows the general utility in using a washed tissue extract as a source of alliinase to prepare pure homologous thiosulfinates from synthetic or pure natural ACSO substrates. Similar yields of reaction would also be expected if mixtures of synthetic ACSO are used, based on fundamental enzyme kinetics. It is not necessary to use immobilized or partially isolated forms of the alliinase and this process can be scaled up simply by using more tissue (or tissue solids) to obtain greater capacity/levels of alliinase. The >98% purity of the homologous thiosulfinates was confirmed by HPLC (FIG. 4) and $H^1$-NMR.

EXAMPLE 6

In this Example, garlic tissues and onion tissues were used in the processes of the present disclosure to prepare thiosulfinates.

Figure 5:
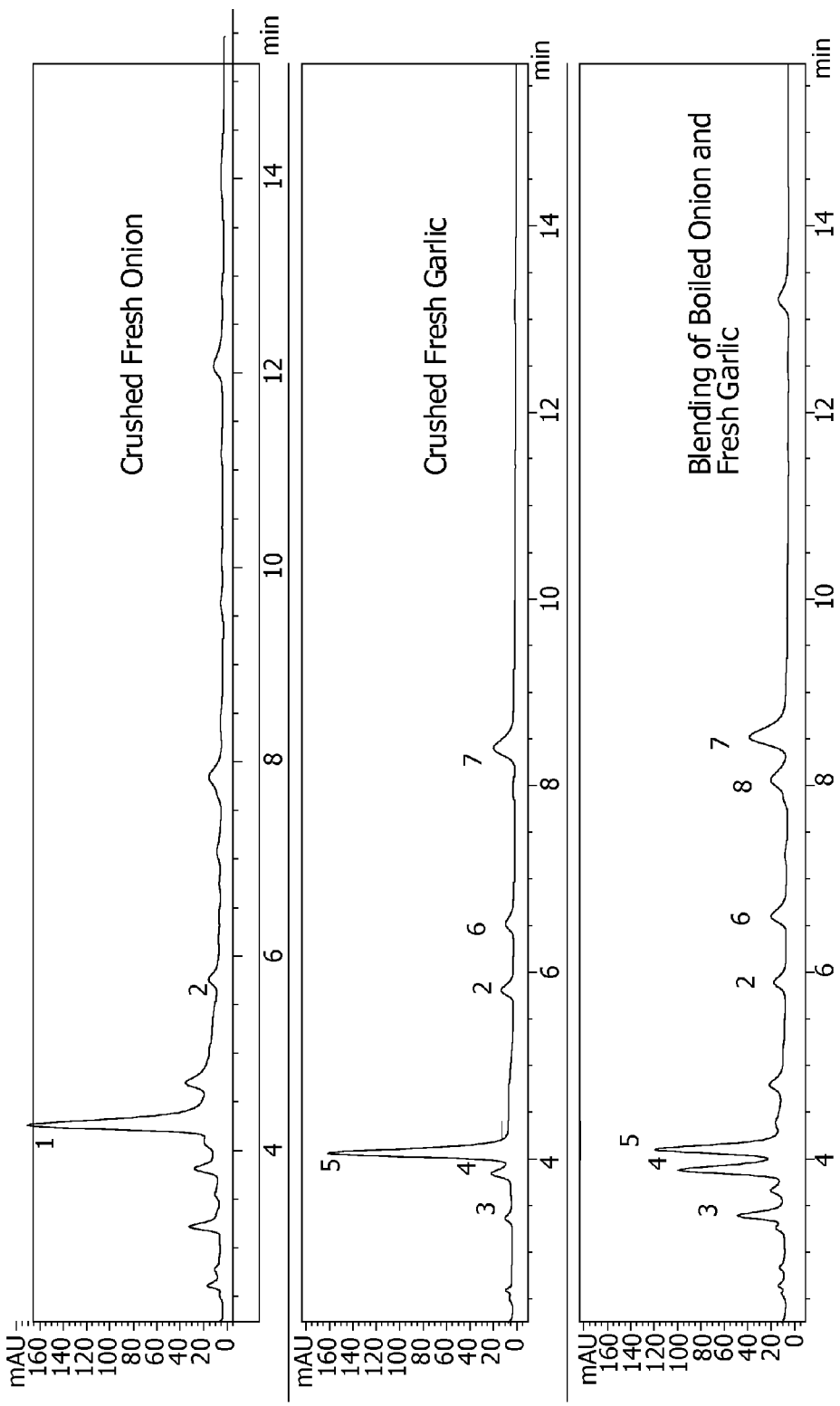
FIG. 5 depicts the organosulfur profile of crushed onions, garlic and blending of boiled onion and garlic as analyzed in Example 6.

A preferred ACSO source is onion bulb tissue, which is rich in 1-PeCSO but also contains alliinase/LF synthase, requiring that this intrinsic enzyme activity be destroyed. An example of preparing such a natural ACSO source follows. About 200 g peeled white onions are cut into quarters, and bulb segments are separated and then placed in boiling water for 4 minutes. Tissue is recovered, allowed to cool at ambient (room) temperature, and then homogenized with 10 g fresh garlic for 1-2 minutes. The mixture is incubated at ambient (room) temperature for 60 minutes, filtered through a cheesecloth, and the filtrate extracted with 100 ml $CH_2Cl_2$. Phase separation yields the solvent extract containing the thiosulfinates which is then dried over anhydrous $MgSO_4$, followed by evaporation of solvent under a gentle air or nitrogen stream at ambient (room) temperature, yielding a thiosulfinate-rich residue. Typical evolution of thiosulfinates using this process is illustrated in FIG. 5, which shows the HPLC profile in this tissue blend (lower panel), compared to the homogenates of raw onion bulb (top panel) or garlic clove (middle panel) tissues alone as references. The PTSO (peak #1) is the principle product evolved in crushed onion, and it is virtually absent in homogenized garlic and the tissue blend. The principal thiosulfinate in garlic is the di-2-propenyl species (allicin, peak #5), and 1-propenyl-containing thiosulfinates comprise <5% of the total thiosulfinates present. In the tissue blend, the proportion of 1-propenyl-containing thiosulfinates was nearly 50% of the total, and this was largely conferred by the designed process serving to retain 1-propenyl equivalents derived from onion in the thiosulfinate pool instead of allowing PTSO to form.

EXAMPLE 7

In this Example, a washed garlic homogenate was prepared to be essentially free of thiosulfinates as in Example 5, and then boiled onion tissue as prepared in Example 2 was combined at a volume:mass ratio of approximately 1:20. After 40-60 minutes incubation, thiosulfinates were extracted in $CH_2Cl_2$, and reconstituted in water after evaporation of the solvent. HPLC analysis revealed that there were no/trace thiosulfinates eluting at the retention times shown for the samples in FIG. 5. Later eluting peaks revealed the major components in this isolate to be zwiebelanes (FIG. 2), and bis-sulfine, although there were other minor components. This shows the utility of the methods for the facile preparation of the di-1-propenyl thiosulfinate-derived species.

EXAMPLE 8

In this Example, chives were used as the allinase-bearing source to substitute for garlic and combine with boiled onion tissue under the same conditions as Example 6. HPLC analysis of the resulting thiosulfinate preparation showed few of the peaks present in the samples shown in FIG. 6, and no LF peak. The dominant thiosulfinates detected were methyl/propenyl and dimethyl species.

EXAMPLE 9

In this Example, various changes were made to the processes of the present disclosure and the profiles of the resulting thiosulfinates were analyzed.

Figure 6:
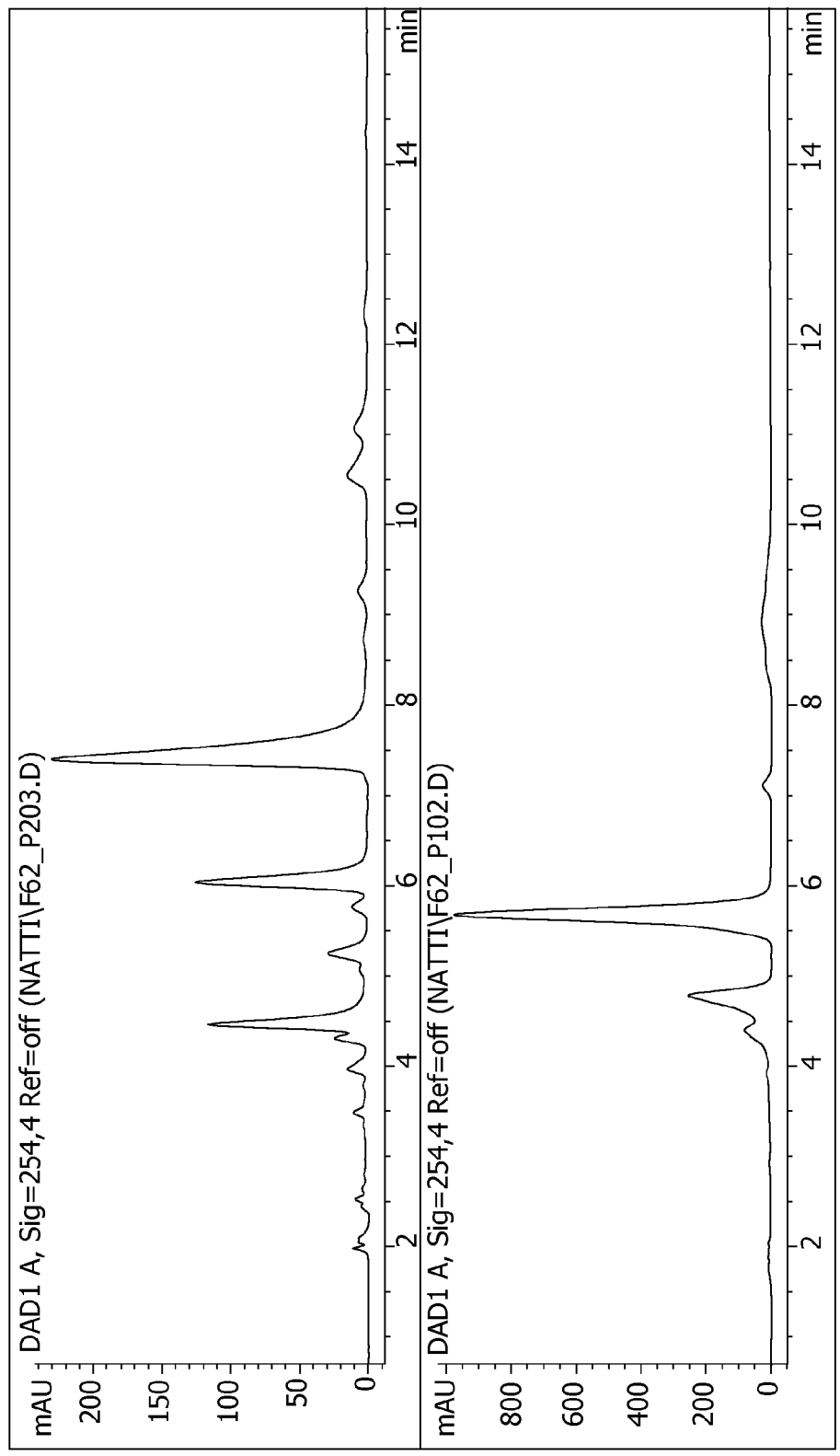
FIG. 6 depicts thiosulfinate evolution in washed garlic preparations as prepared in Example 9.

To begin, garlic homogenate was prepared and then washed/extracted with solvent, after which synthetic ECSO was added and the reaction allowed to proceed for 30-40 minutes (as in Example 1). The thiosulfinate profile after this stage (FIG. 6, bottom panel) was similar to that observed in FIG. 3. A third stage of reaction evoked by adding boiled onion tissue, homogenization and incubation for an additional 40-60 minutes lead to a unique profile of thiosulfinates, which were also lacking in LF (FIG. 6, upper panel). Diethyl thiosulfinate was almost completely transformed, as were most of the residual garlic species, to mixed thiosulfinate species rich in 1-propenyl groups (peaks at 4 and 6-8 minutes) derived from the boiled onion tissue.

EXAMPLE 10

In this Example, mixed disulfide conjugates were prepared using the processes of one embodiment of the present disclosure.

To begin, a garlic homogenate was allowed to incubate for an extended period of time, approximately 40-60 minutes, and then "washed" with EtOAc to be essentially free of residual thiosulfinates. Then a fixed amount of individual ACSO was dissolved in 10 ml water and added to 90 ml of the washed garlic homogenate. After subsequent incubation for 40-60 minutes, the evolved thiosulfinates were extracted by $CH_2Cl_2$, subjected to solvent evaporation and reconstitution in water.

Figure 7:
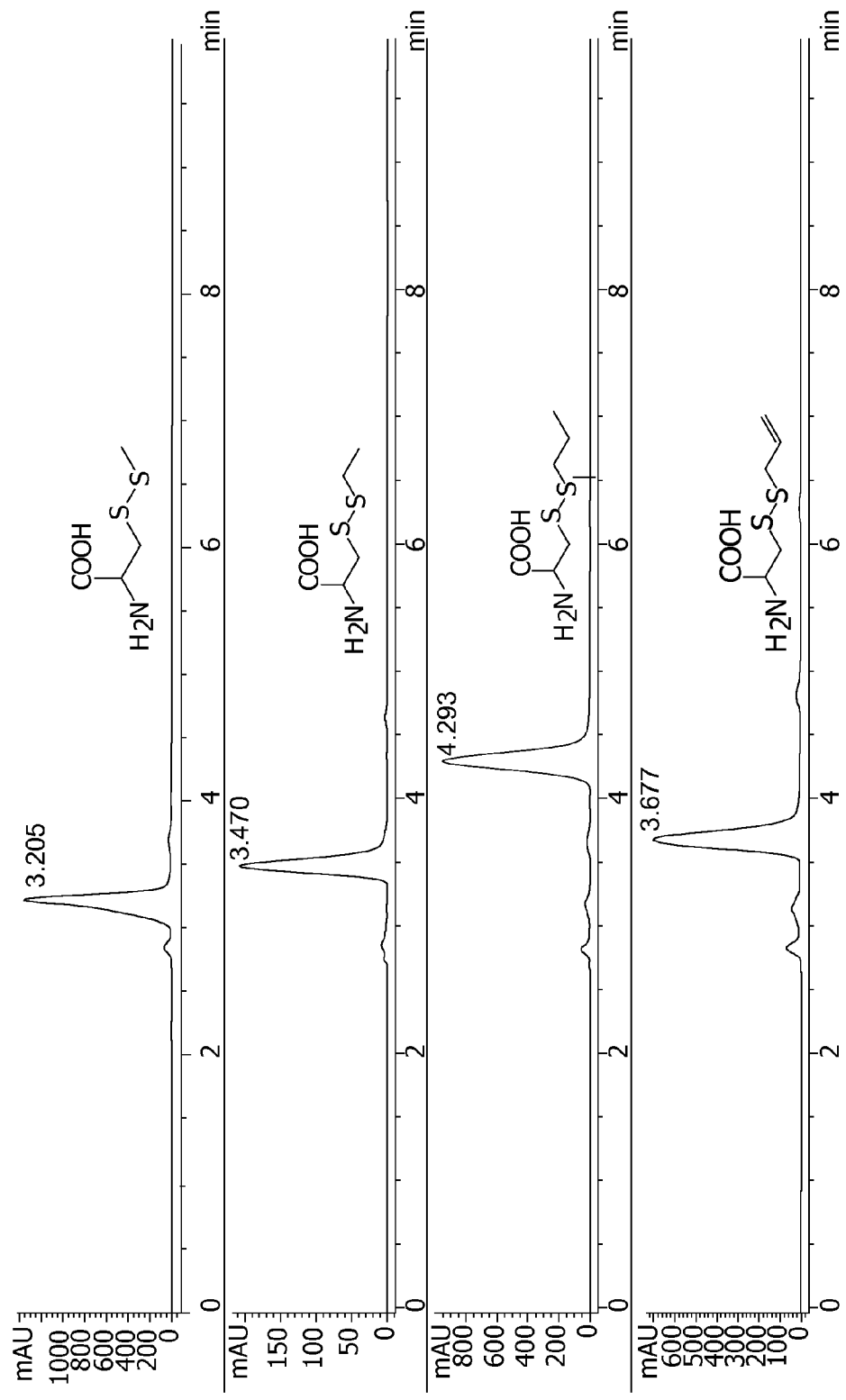
FIG. 7 depicts the HPLC analysis of CySSR prepared in Example 10.

Then 1.5-2.0 moles of cysteine (CYS) or glutathione (GSH) dissolved in water was added for each 1.0 mole thiosulfinate, and the reaction mixture stirred at ambient (room) temperature for 1-2 hours. HPLC analysis of the solution phase of the reaction mixture (FIG. 7) showed that the prepared conjugates CySSR (R=methyl, ethyl, propyl and allyl) using the thiosulfinates generated by washed garlic homogenate were >95% pure, with no further purification. $^1$H-NMR analysis showed the major impurity in the reaction mixture was unreacted starting material, CYS. The preparation of the glutathione mixed disulfide conjugates (GSSR) gave similar results. For larger scale and elevated concentrations of reactants, the accumulation of conjugates proceeds to a point that exceeds their solubility in water. This facilitates recovery of the conjugate product mixture as a precipitate by simple filtration. Alternatively, the entire conjugation reaction mixture can be dried. In both cases, washing the residue with an appropriate organic solvent will remove any residual thiosulfinates.

EXAMPLE 11

In this Example, mixed disulfide conjugates were prepared using the processes of one embodiment of the present disclosure.

Figure 8:
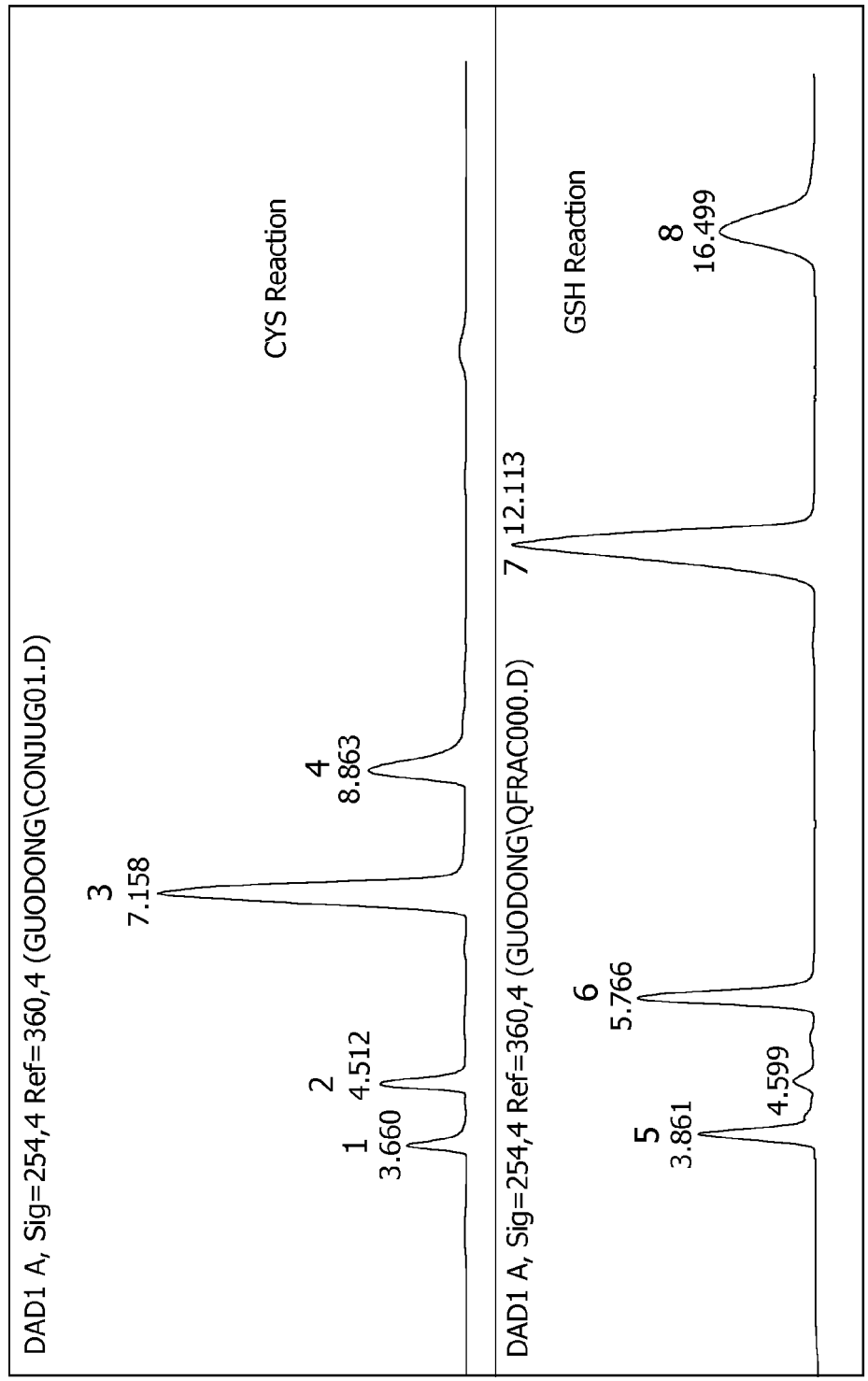
FIG. 8 depicts the HPLC analysis of CySSR and GSSR as prepared in Example 11.

Using a similar approach as was described in Example 9, about 200 g peeled white onions were sectioned and segmented prior to boiling in water for approximately 4 minutes. The tissue was drained, allowed to cool to ambient (room) temperature, and then homogenized with 10 g fresh garlic for approximately 1-2 minutes. The mixture was then incubated at ambient (room) temperature for 40-60 minutes, filtered through cheesecloth, and the filtrate was then extracted with 100 ml $CH_2Cl_2$. After phase separation, the solvent extract containing the thiosulfinates was evaporated to dryness at ambient (room) temperature, yielding a thiosulfinate-rich residue that was resuspended in water. Then 1.5-2.0 moles of cysteine (CYS) or glutathione (GSH) dissolved in water was added for each 1.0 mole thiosulfinate, and the reaction mixture stirred at ambient (room) temperature for 1-2 hours. HPLC analysis in FIG. 8 shows the profile of prepared conjugates of CySSR and GSSR chemotypes (R=methyl, ethyl, propyl and allyl) using the thiosulfinates generated by the tissue blend, with no further purification. All the major R groups of *Allium* thiosulfinates (ethyl and propyl being least abundant and not detected in the samples) were present among the major species of CySSR and GSSR chemotypes. The identity of each peak on HPLC was confirmed by co-elution of synthetic standard conjugates and LC-MS analysis.

EXAMPLE 12

In this Example, the thiosulfinate, CySSPe, was chemically synthesized using one embodiment of the processes of the present disclosure.

Initially, sodium (2 g) was added to 200 mL MeOH in a reflux apparatus, stirred until the sodium was dissolved, and then 25 g of triphenylmethanethiol (TrSH) was added. The reaction mixture was refluxed for 1 hour, 10 mL allyl bromide was then added, and the mixture was refluxed for another 2 hours. The solution was allowed to cool, 19 g of particulate material, trityl allyl sulfide (TrSAll), was obtained by filtration using filter paper, and it was used directly for the next step without any purification. tert-BuOK (11 g) was added to a solution of 19 g of TrSAll in 100 mL anhydrous tetrahydrofuran (THF) and 200 mL tert-BuOH, and the reaction mixture was stirred at 20-22° C. overnight. The solvent in the reaction mixture was removed by rotary evaporation, water and $CH_2Cl_2$ was added to the residue, and the product was extracted into the $CH_2Cl_2$ phase. Trityl 1-propenyl sulfide (TrSPe) was obtained as a white color powder by purification of the $CH_2Cl_2$ extract on a silica gel column eluted with 10% $CH_2Cl_2$ in hexane.

Bromine (0.13 mL) was then added to a suspension of 1.2 g of Boc-cystine in 50 mL $CH_2Cl_2$ at −80° C. (maintained with a dry ice-ethanol bath), and stirred at −80° C. for 10-15 minutes. Then 1.7 g of TrSPe dissolved in 10 mL $CH_2Cl_2$ was added, and the mixture was stirred for another 30 min at 20-22° C. The reaction mixture was purified on a silica gel flash column eluted with 5% methanol in $CH_2Cl_2$ to provide 0.32 g (yield 20%) of Boc-CySSPe as a yellow oil. To remove the Boc-group, 0.84 mL trifluoroacetic acid (TFA) was added to a solution of 0.32 g Boc-CySSPe in 0.84 mL $CH_2Cl_2$ at 0° C. and stirred at 0° C. for 1.5 hours. Solvent was removed from the reaction mixture under vacuum, and the residue was washed with $CH_2Cl_2$, allowing CySSPe to be obtained as a white solid. The reaction scheme is shown below.

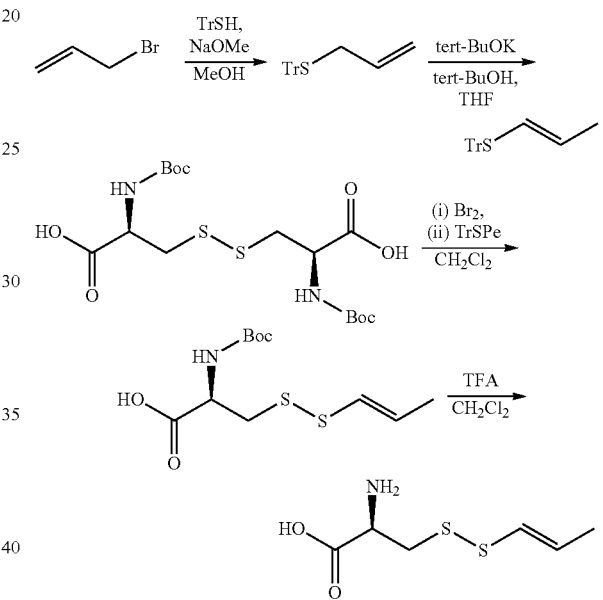

The structure was confirmed by comparing NMR data with a published result (Hiramitsu, and Sakamoto, 1990). $^1$H NMR ($D_2O$, 500 MHz): δ 4.35 (dd, J=4.0, 8.0 Hz, 1H, H-2), 3.37 (dd, J=4.0, 15.5 Hz, 1H, H-3a), 3.21 (dd, J=8.0, 15.0 Hz, 1H, H-3β), 6.17 (m, 2H, H-4 and H-5), 1.81 (m, 3H, H-6). HR-ESI-MS, m/z [M+H]$^+$ at 194.0308 (calcd 194.0309), [M−H]$^-$ at 192.0166 (calcd 192.0153).

EXAMPLE 13

In this Example, thiosulfinates as prepared as organic solvent extracts as described herein were used in reactions with lipophilic SH reactants to prepare chemical synthons.

Figure 9:
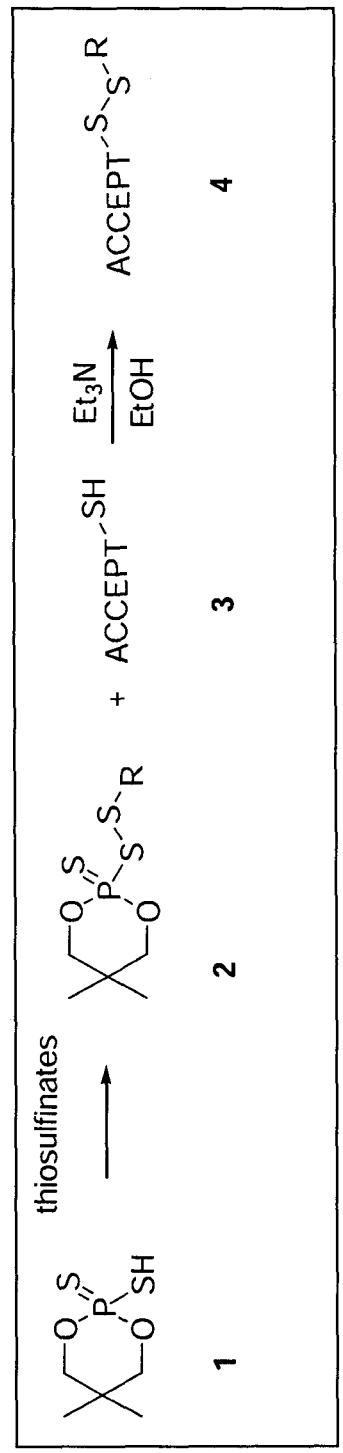
FIG. 9 depicts the reaction mechanism for the preparation of a lipophilic alkylthiolate donor as the synthon for chemical syntheses.

As shown in FIG. 9, if compound (I) is added in >2 molar equivalents to the solvent extract containing thiosulfinates, it reacts to form a mixed disulfide conjugate (compound 2) which carries the mercapto R-groups originating from thiosulfinates (FIG. 9). Since the reaction can take place in organic solvent, the advantage is that thiosulfinate organic extracts do not have to be evaporated, at risk of losing thiosulfinates by volatility, prior to reaction with compound 1. Compound 2 is stable, can be recovered by evaporation, solvent partitioning or crystallization, and thus can be used as a reservoir for thiosulfinate R groups for further synthetic purposes. These thiolate groups on compound 2 can be transferred to other thiol compounds ("ACCEPT-SH") to prepare asymmetric disulfides, including conjugates of CYS and GSH.

EXAMPLE 14

In this Example, thiosulfinates as prepared as organic solvent extracts as described herein were used to derivatize the SH-containing component Captopril.

Figure 10:
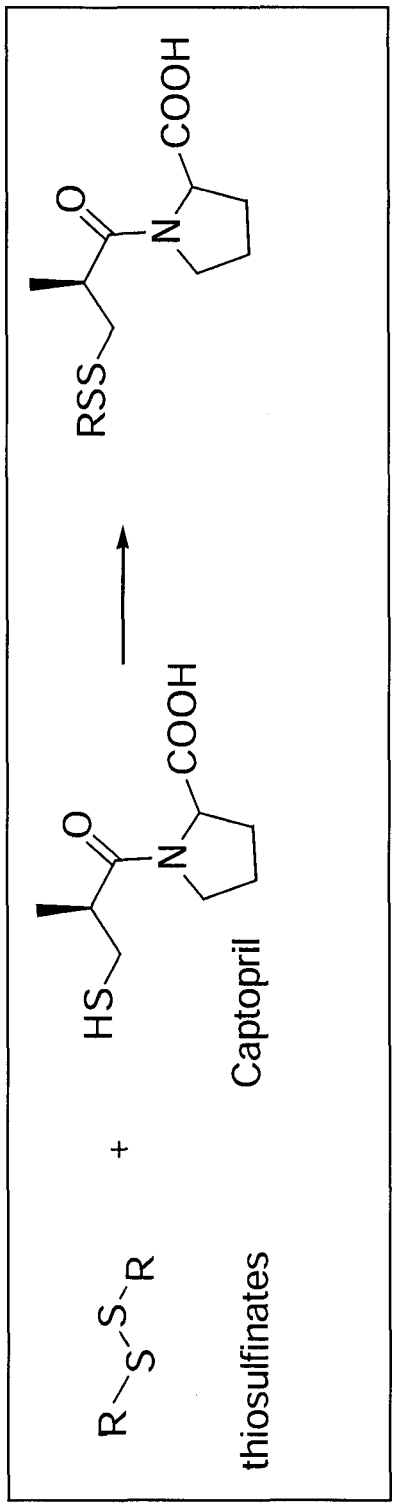
FIG. 10 depicts the reaction scheme for the preparation of the mixed disulfide conjugates prepared from Captopril and thiosulfinate(s).

Approximately 1.5-2.0 molar equivalent of Captopril was added to the thiosulfinate preparation, yielding the mixed disulfide conjugate of Captopril and thiosulfinate(s) (FIG. 10). Common procedures of solvent evaporation, partitioning or recrystallization can be used to purify and recover the modified drug or reagent.

It should be understood by one skilled in the art that other SH-containing components could be used in substitution to Captopril without departing from the scope of the present disclosure.

EXAMPLE 15

In this Example, individual species of the CySSR and GSSR conjugates were stored dry for over a year at −18° C. with intermittent warming to 21-23° C. for about two days every 3-4 weeks. $^1$H-NMR analysis revealed essentially no change in the proton spectrum from the beginning to the end of the storage study, indicating negligible decay of all of the conjugates.

EXAMPLE 16

In this Example, the enzyme-inducing activity of mixed disulfide conjugates as prepared using processes of the present disclosure was analyzed.

Figure 11:
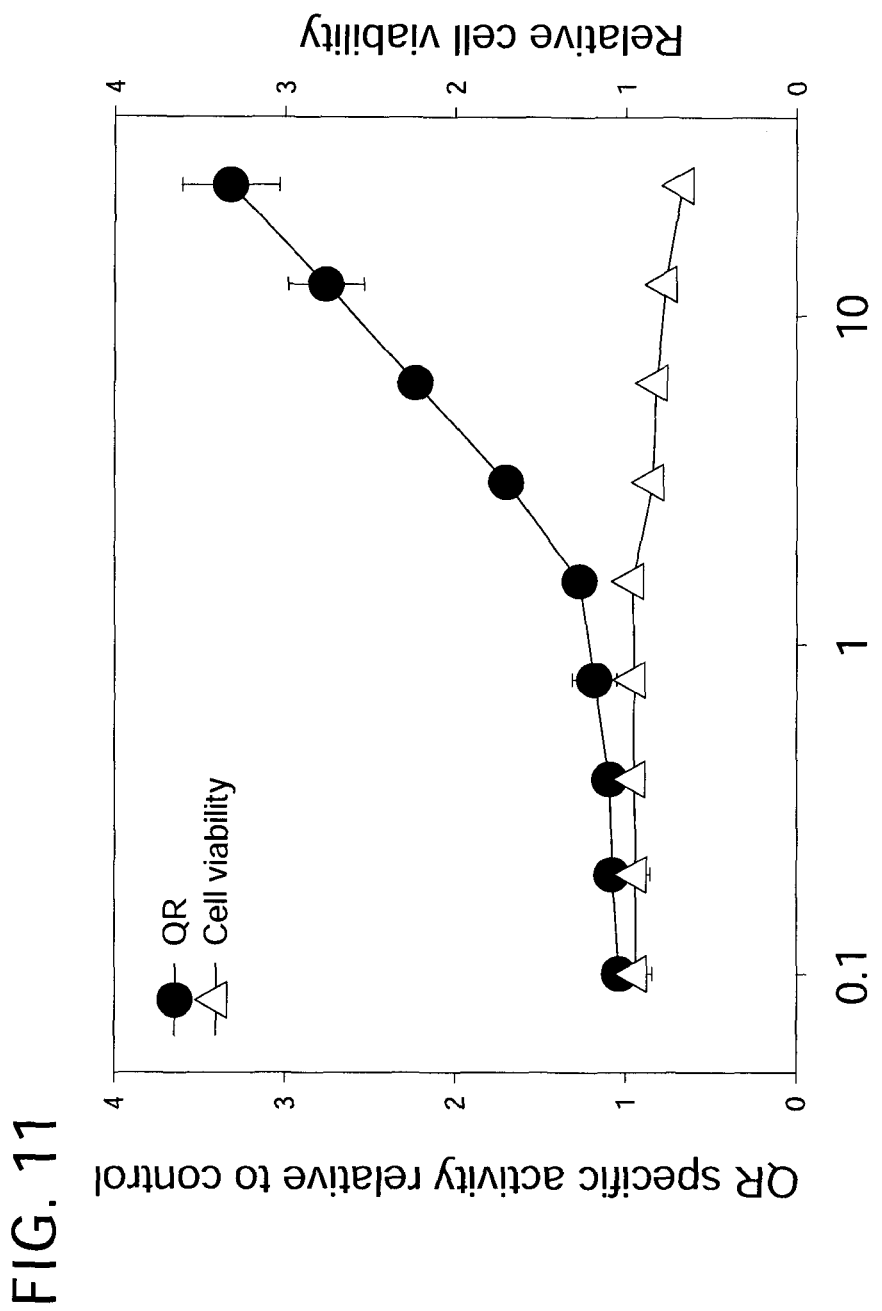
FIG. 11 depicts the QR induction by CySSPe in Hepa 1c1c7 cells as analyzed in Example 16.

Specifically, the mixed disulfide conjugates as prepared similar to the pure conjugates of Example 10 or purified from mixtures prepared in Example 11 were used with the Hepa 1c1c7 cell line as disclosed in Prochaska, et al., 1992. Each conjugate was tested over a dose range and increases in quinone reductase (QR) activity was used as a biomarker for phase II enzyme induction, an established mechanism of cancer chemoprotection. The dose where there was a doubling of QR (CD value) was estimated and used as a relative measure of inducer potency, with lower levels being more potent. Results were considered valid as long as cell viability in the assay was >50% as recommended by the established protocol. Typical experimental results are shown for the CySSPe conjugate (FIG. 11), and summary results are provided for all conjugates in terms of relative potency (CD values) for QR induction (Table 8). All mixed disulfide conjugates were active QR inducers with the unsaturated species of conjugates being more potent that saturated species, and with GSSR species being generally more potent than CySSR species on a molar concentration basis.

TABLE 8

QR Inducing Potency of CYS and GSH conjugates of thiosulfinates (CySSR/GSSR).

| Compound | CD values (µg/ml) | (µM) |
|---|---|---|
| CySSM | 89 | (530) |
| CySSE | 76 | (420) |
| CySSP | 92 | (470) |
| CySSPe | 4.8 | (25) |

TABLE 8-continued

QR Inducing Potency of CYS and GSH conjugates of thiosulfinates (CySSR/GSSR).

| Compound | CD values (µg/ml) | (µM) |
|---|---|---|
| CySSA | 26 | (130) |
| di-1-propenyl derivatives* | 15 | NA |
| GSSM | 87 | (250) |
| GSSE | 72 | (200) |
| GSSP | 73 | (190) |
| GSSPe | 5.3 | (14) |
| GSSA | 33 | (87) |

*Prepared as in Example 7. These were not pure, so there was no µM equivalent that could be estimated, and they were not conjugated with either CYS or GSH.

EXAMPLE 17

In this Example, disulfide conjugates of whey protein isolate were prepared using the processes of one embodiment of the present disclosure.

Figure 16:
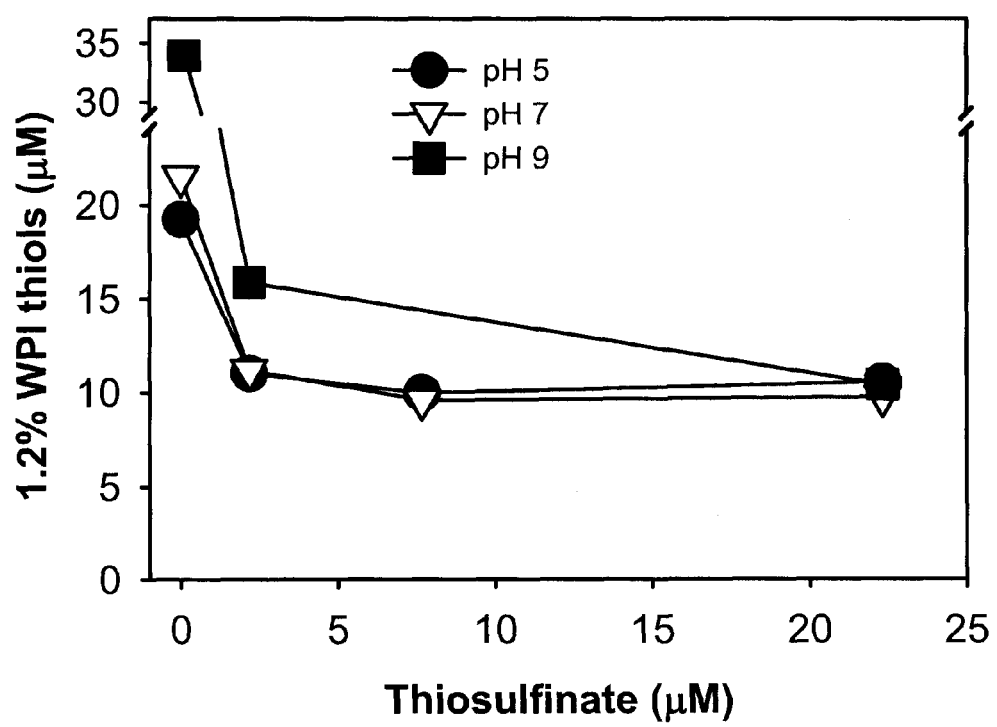
FIG. 16 depicts the effect of pH on conjugation reactions of whey protein isolate (WPI) and thiosulfinates as analyzed in Example 17.

Specifically, native whey proteins (1.2%) were combined with thiosulfinates in the absence of exogenous buffer at pH of 5, 7 and 9 prepared by adjusting pH of the proteins solutions directly with 1 N HCl or 1 N NaOH. A range of thiosulfinate levels were added to different portions of the protein solution and allowed to react for 10 minutes before measuring loss of protein thiol groups after the reaction. About 50% of the protein thiols were depleted at thiosulfinate levels of <5 µM where the molar ratio of thiosulfinate:protein-SH groups was about 1:2 (FIG. 16). The balance of the protein thiols remained unreacted even as thiosulfinate levels were increased to about equimolar with protein-SH (theoretically, ~2× molar excess for conjugation reactions). This shows that some protein-SH groups are readily available while others are recalcitrant to conjugation reactions in native proteins. This Example also shows that exposure of whey protein isolate to pH 9 unmasked protein-SH groups relative to the levels detected at pH 5 or 7. Conjugation reactions with whey protein isolate can be facilitated over a broad range of pH of 5-9, although not all protein-SH groups were modified in native whey proteins.

EXAMPLE 18

In this Example, disulfide conjugates of egg white protein isolate were prepared using the processes of one embodiment of the present disclosure.

Figure 17:
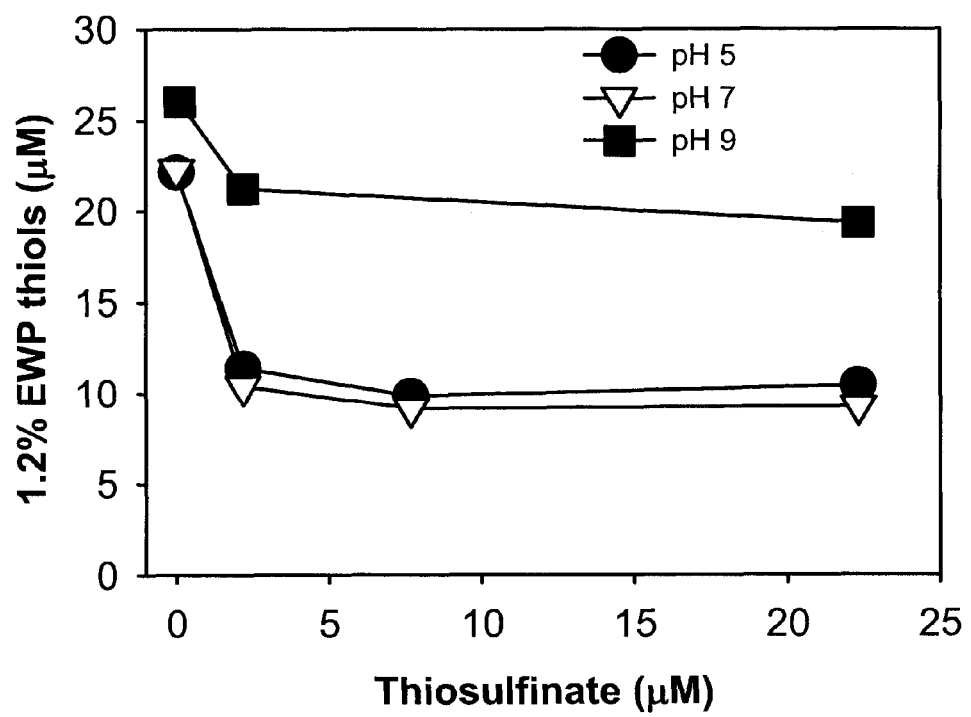
FIG. 17 depicts the effect of pH on conjugation reactions of egg white protein (EWP) and thiosulfinates as analyzed in Example 18.

Specifically, native egg white proteins (1.2%) were combined with thiosulfinates at pH of 5, 7 and 9, reacted and analyzed as in Example 17. About 50% of the protein thiols were depleted at thiosulfinate levels of <10 µM where the molar ratio of thiosulfinate:protein-SH groups was about 1:2 (FIG. 17). The balance of the protein thiols remained unreacted even as thiosulfinate levels were increased to about equimolar with protein-SH (theoretically, ~2× molar excess for conjugation reactions). As with Example 17, this shows that some protein-SH groups are recalcitrant to conjugation reactions in native proteins. This Example also shows that exposure of egg white protein isolate to pH 9 unmasked only a limited amount of protein-SH groups relative to pH 5 or 7. Conjugation reactions with egg white protein isolate can be facilitated over a broad range of pH of 5-9, although pHs 5-7 were more conducive to conjugation reactions than pH 9. Not all protein-SH groups were modified in native egg white proteins.

EXAMPLE 19

In this Example, disulfide conjugates of soy protein isolate were prepared using the processes of one embodiment of the present disclosure.

Figure 18:
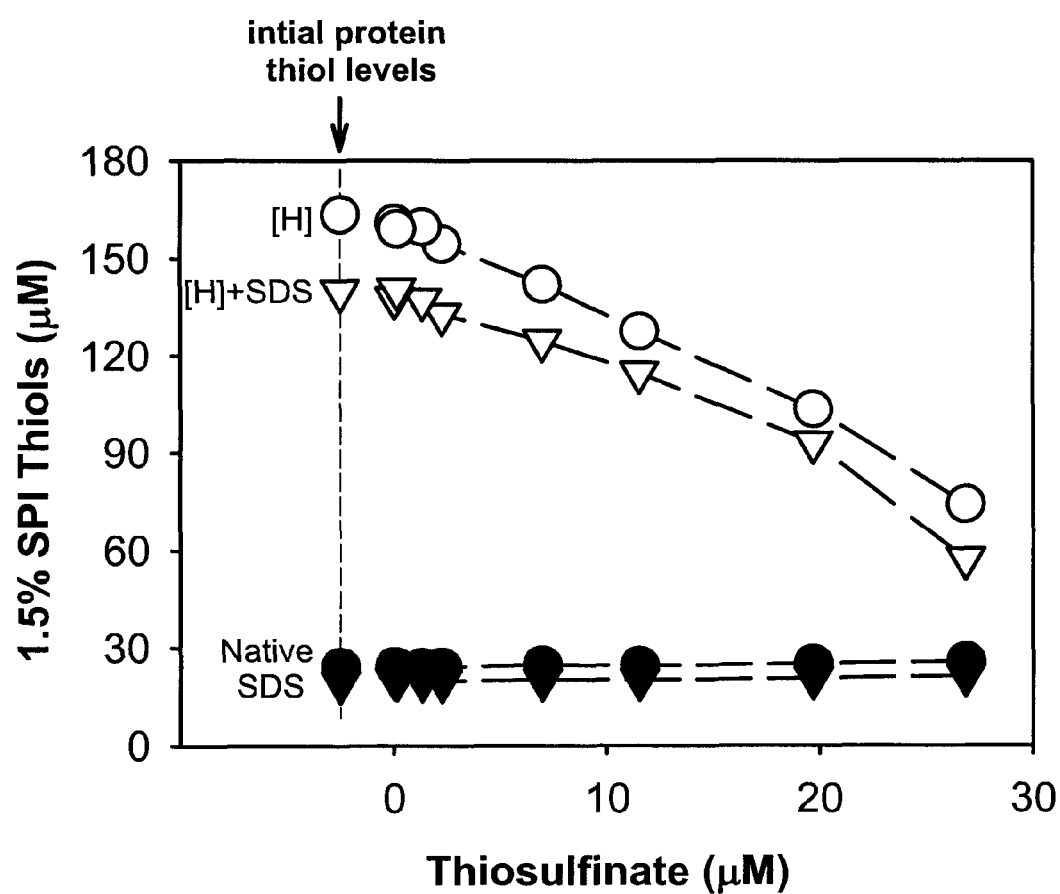
FIG. 18 depicts the effect of reduction ([H]), addition of sodium dodecyl sulfate (SDS), or these treatments combined on conjugation reactions of soy protein isolate (SPI) and thiosulfinates relative to native SPI as analyzed in Example 19.

Specifically, native soy protein isolate was first subject to the following treatments: 1) combined with 1% SDS, 2) reduced by $NaBH_4$, and 3) combined with SDS+$NaBH_4$. Soy protein (1.5%) treated in these manners as well as native soy protein isolates were reacted with thiosulfinates for 10 minutes at pH of 7 and ~20° C., and analyzed for changes in protein-SH levels as evidence of conjugation reactions (FIG. 18). Both native and SDS-treated soy protein isolate exhibited little reaction with thiosulfinates as protein-SH levels practically did not change. Reduction of —SS— in native soy protein isolate yielded ~6-fold increase in protein-SH groups, and reduction in combination with SDS yielded a similar but slightly lower detectable increase in protein-SH levels. Both of these latter treatments facilitated reaction of soy protein-SH groups with thiosulfinates to yield mixed disulfide conjugates (MDC). Thus, reduction of proteins greatly facilitated the preparation of protein MDC by making virtually all cystine+CYS residues in protein available for reaction as CYS with thiosulfinates. SDS alone was not effective for encouraging reaction of soy protein-SH groups with thiosulfinates, and for the reduced protein preparations, bound SDS may hinder/mask reactivity of some protein-SH groups.

EXAMPLE 20

In this Example, disulfide conjugates of a purified egg albumin protein preparation were prepared using the processes of one embodiment of the present disclosure.

Figure 19:
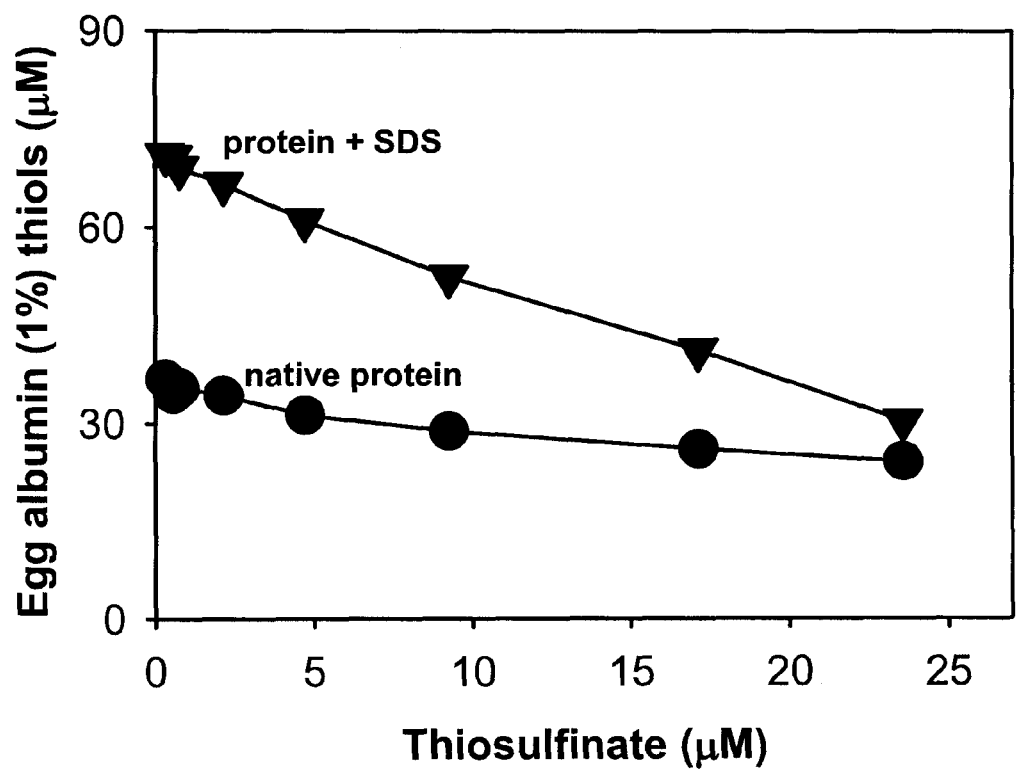
FIG. 19 depicts the effect of the addition of sodium dodecyl sulfate (SDS) on conjugation reactions of purified egg white albumin and thiosulfinates relative to native egg white albumin as analyzed in Example 20.

Specifically, 1% solutions of native egg albumin (untreated) and egg albumin treated with 1% SDS were reacted with thiosulfinates for 10 minutes at a pH of 7 and approximately 20° C. and analyzed for changes in protein-SH levels as evidence of conjugation reactions (FIG. 19). Both native and SDS-treated protein exhibited declines in protein-SH groups with increasing thiosulfinate levels, evidence of the formation of MDC. SDS treatment unmasked protein-SH groups in albumin, doubling the level of protein-SH groups and MDC formation possible. SDS was effective as a surfactant to cause unfolding of egg albumin and exposure of protein-SH for reaction with thiosulfinates.

EXAMPLE 21

In this Example, disulfide conjugates of whey protein isolate were prepared using the processes of one embodiment of the present disclosure.

Figure 20:
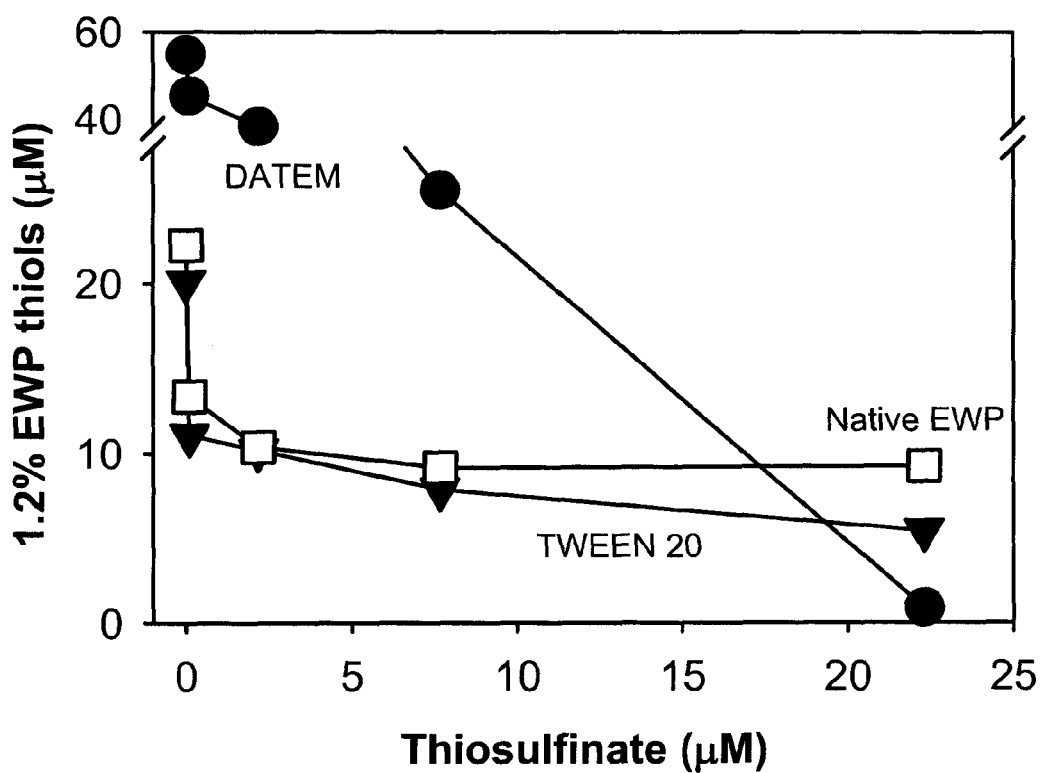
FIG. 20 depicts the effect of the addition of diacetyltartaric acid esters of monoacylglycerols (DATEM) and polyoxyethylene sorbitan laurate (TWEEN 20) on conjugation reactions of egg white protein (EWP) and thiosulfinates relative to native EWP as analyzed in Example 21.

Specifically, whey protein isolate (1.2%) was combined with 1% DATEM or 1% TWEEN 20 for ~30 minutes prior to reaction with thiosulfinates for 10 minutes at pH of 7 and ~20° C., and analyzed for changes in protein-SH levels as evidence of conjugation reactions. Both emulsifiers facilitated reactivity of whey protein-SH groups with thiosulfinates to yield MDC relative to the native protein (FIG. 20). TWEEN 20 facilitated further reactivity of recalcitrant protein-SH groups below 10 µM residual levels compared to the native protein without emulsifier. The inclusion of DATEM with whey protein solutions increased the availability (detectability) of protein-SH groups from ~20 µM to 55 µM. This was likely caused by perturbation/unfolding of the protein to unmask buried protein-SH groups. In addition, DATEM facilitated a virtually complete derivatization of protein-SH groups by thiosulfinates, leading to low residual protein-SH levels at the highest level of thiosulfinates tested.

EXAMPLE 22

In this Example, disulfide conjugates of egg white and whey protein isolates were prepared using the processes of one embodiment of the present disclosure.

Figure 21A:
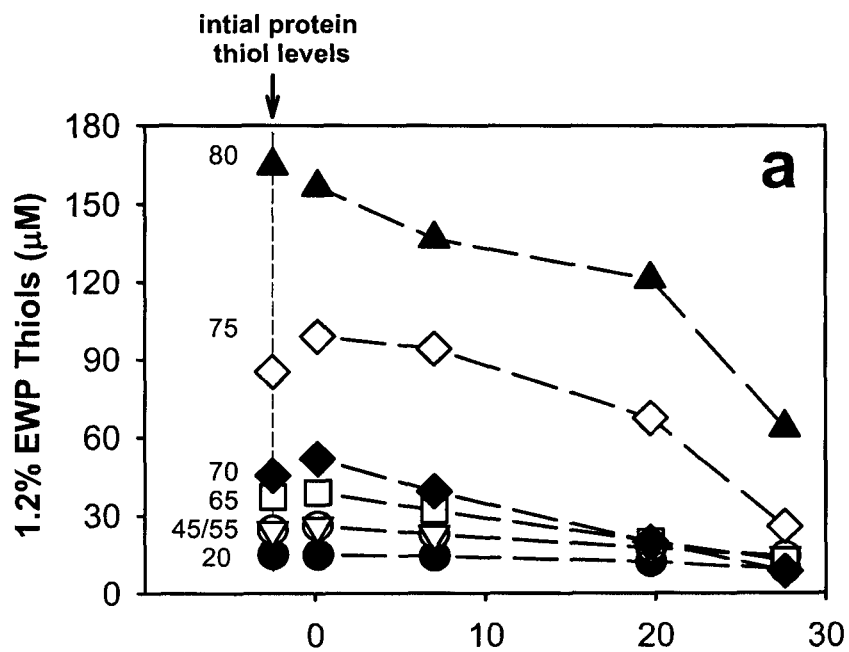
FIG. 21 depicts the effect of pre-heating of (A) egg white protein (EWP), and (B) whey protein isolate (WPI) on conjugation reactions of thiosulfinates after cooling and reaction at 20° C. relative to native SPI as analyzed in Example 22.
Figure 21B:
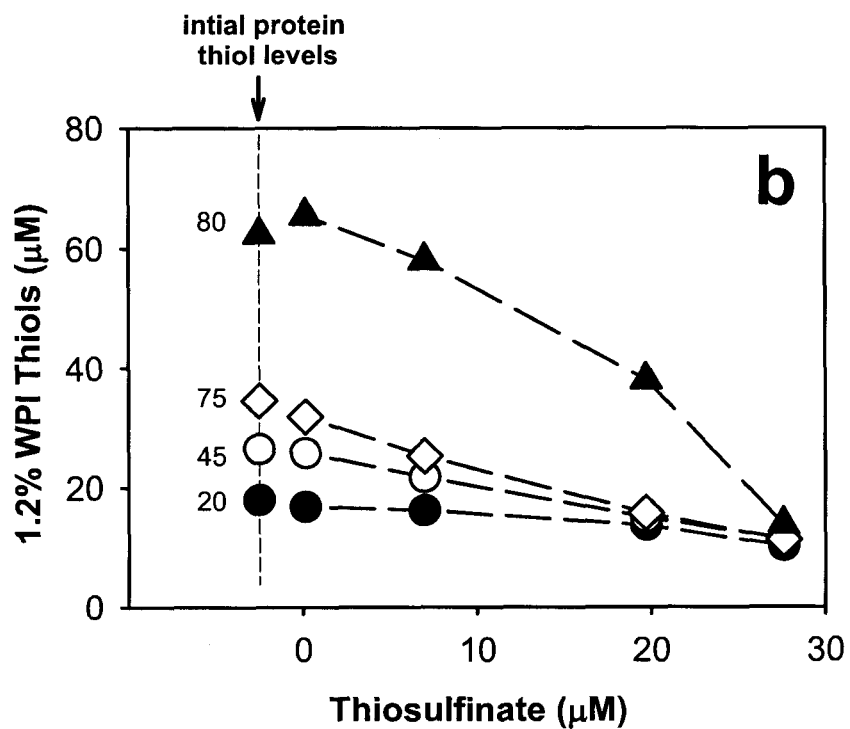

Specifically, egg white and whey protein isolates were pre-treated at various temperatures up to 80° C. prior to cooling to 20° C. and combined with thiosulfinates to react for 10 minutes at pH 7. Increasing the temperature of pre-treatment led to increased exposure of protein-SH groups for both egg white and whey protein preparations (FIGS. 21A and B). Increasing elevation of the temperature likely caused progressive protein unfolding which was preserved upon cooling to the reaction temperature of 20° C. Pre-heating of proteins allowed for a greater capacity to form MDC with thiosulfinates. Egg white proteins exhibited obvious coagulation at 70° C., whereas whey proteins did not begin to aggregate until 80° C. Thus, even coagulated/aggregated proteins could react to form MDC with thiosulfinates, and this implies that solid state reactions could occur between solution phase thiosulfinates with proteins not in solution.

EXAMPLE 23

In this Example, disulfide conjugates of egg white and whey protein isolates were prepared using the processes of one embodiment of the present disclosure.

Figure 22A:
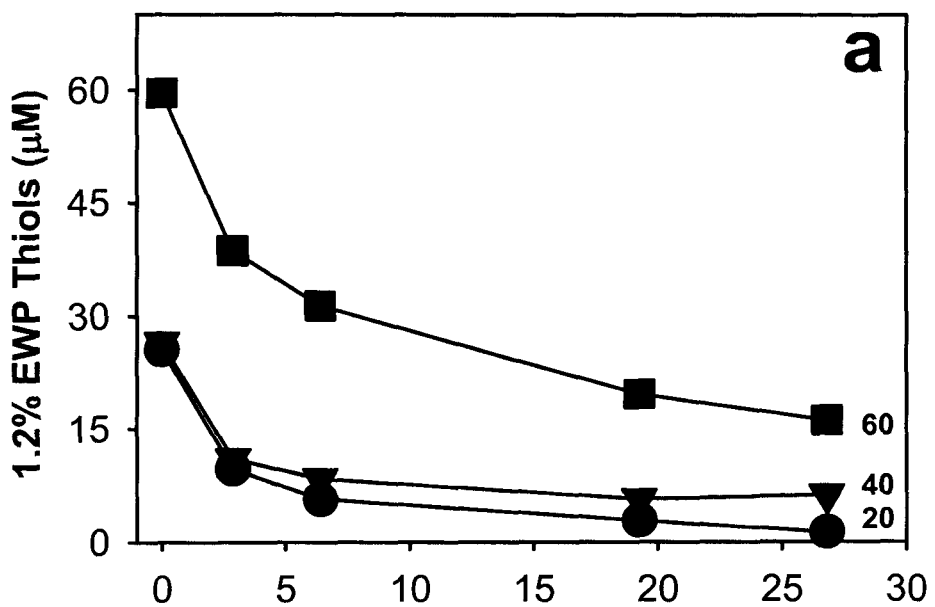
FIG. 22 depicts the effect of reaction temperature on the extent of conjugation reactions of thiosulfinates with (A) egg white protein (EWP), and (B) whey protein isolate (WPI) as analyzed in Example 23.
Figure 22B:
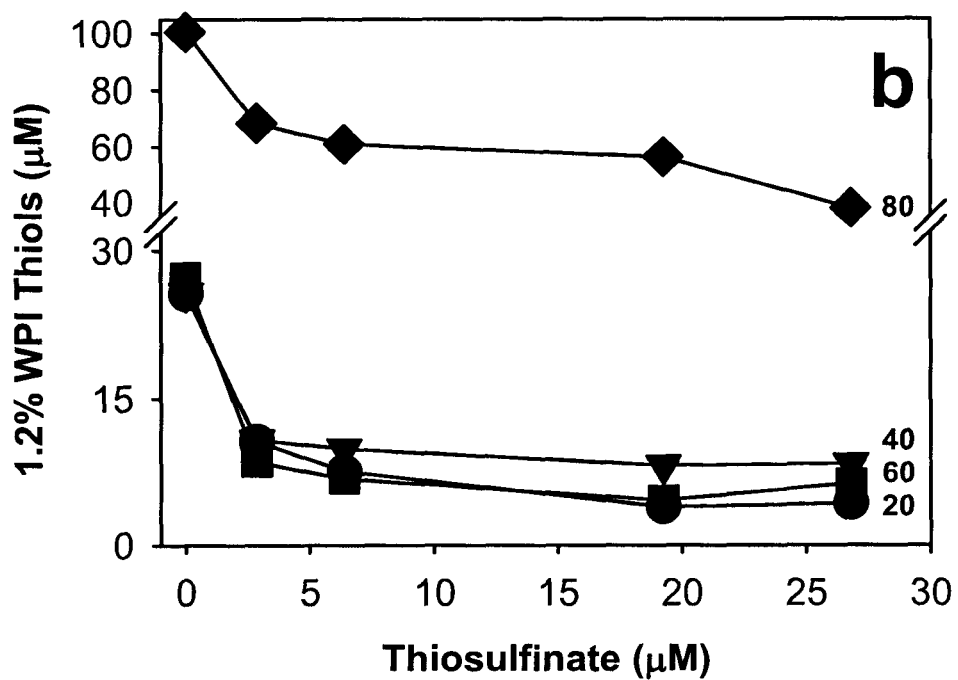

Specifically, egg white and whey protein isolates were reacted with thiosulfinates at various temperatures up to 80° C. for 10 minutes at pH 7 (FIGS. 22A and 22B). Increasing reaction temperature had little effect on the extent of reaction of protein-SH groups with thiosulfinates between 20-60° C. for whey proteins and 20-40° C. for egg white proteins. When protein coagulation was evident (60° C.+ for egg whites and 80° C. for whey proteins), greater availability or exposure of protein-SH reaction with thiosulfinate was observed (this was also shown in a Example 22). However, the decrease in levels of protein-SH groups at each thiosulfinate level used were similar for all reaction temperatures. Thus, temperature influenced availability of protein-SH groups for reaction, but had only marginal impact of extent of reaction for the 10-minute reaction period. A limitation of increased reaction temperature is that thiosulfinates decayed by 27% at 60° C. and 34% at 80° C. when tested alone under the reaction conditions examined.

EXAMPLE 24

In this Example, disulfide conjugates of solubilized keratin were prepared using the processes of one embodiment of the present disclosure.

Figure 23:
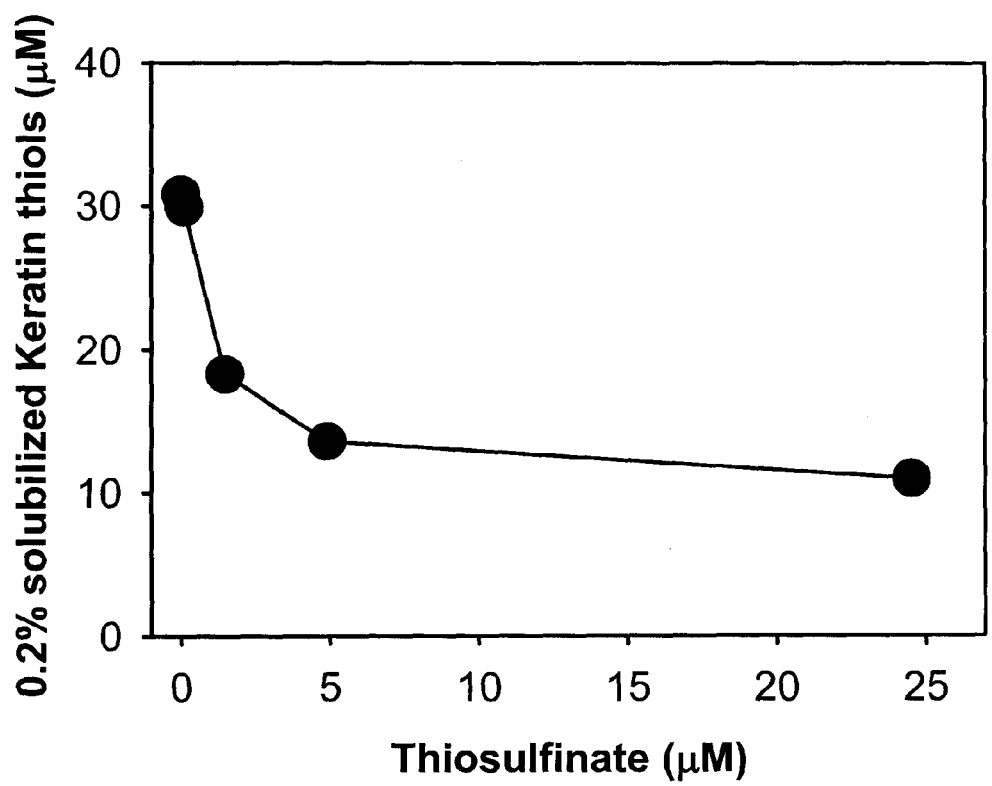
FIG. 23 depicts the extent of conjugation reactions between solubilized chicken feather keratin and thiosulfinates as analyzed in Example 24.

Specifically, cleaned and ground chicken feather keratin obtained as Featherfiber® was solubilized in 8 M urea and 0.5 N NaOH for about 1 hour, followed by reduction with $NaBH_4$ for 30 minutes at pH ~10. A diluted keratin (0.05%) was reacted with thiosulfinates at 20° C. and pH 7.0 for 10 minutes (FIG. 23). The decline in protein-SH groups with increasing thiosulfinate indicated facile reaction to yield MDC. As with other proteins, the extent of reaction with thiosulfinate was biphasic, with the easiest reacting protein-SH groups declining at the low range of thiosulfinates used, followed by more recalcitrant reacting protein-SH groups declining at the upper range of the thiosulfinate levels examined. Thus, it is necessary to use a molar excess of thiosulfinates in many cases to approach maximal or near-capacity of MDC.

EXAMPLE 25

In this Example, solid state reactions of protein with thiosulfinates dissolved in ethyl acetate were used to prepare disulfide conjugates. About 4.1 μmol thiosulfinates comprising a portion of the diluted original ethyl acetate of the *Allium* tissue homogenate were combined with 1.7 μmol of protein-SH as powder egg white protein dispersed in the solvent. After about 1 hour reaction at 20° C., 21% decline of protein-SH was observed through conjugation reaction with thiosulfinate. This application circumvents the need to evaporate solvent used for thiosulfinate extraction as well as copious water resources for handling soluble protein systems. This Example constitutes an extension of the solid phase reaction concept observed in Example 22.

EXAMPLE 26

In this Example, disulfide conjugates of a enzymatically hydrolyzed whey protein isolates can be prepared using the processes of one embodiment of the present disclosure.

Specifically, native proteins can be hydrolyzed at 37° C. by the enzymes pepsin for 4-6 hours at pH ~2 and trypsin for 1-4 hours at pH ~7.5. Protein preparations can be treated with the reducing agent $NaBH_4$ to convert —S—S— groups to —SH groups. Peptides can be passed through a thiopropyl Sepharose column activated with dithiodipyridine and infused with peptides to covalently capture peptide-SH species while non-cysteine containing peptides will flow through the column. Peptide-SH species can be eluted from the column by β-mercaptoethanol. Eluted thiol-containing peptides can then be introduced with thiosulfinate preparations in buffered aqueous media to prepare protein-mixed disulfide conjugates.

EXAMPLE 27

In this Example, the anti-inflammatory activity of the mixed disulfide conjugates was analyzed.

Figure 12:
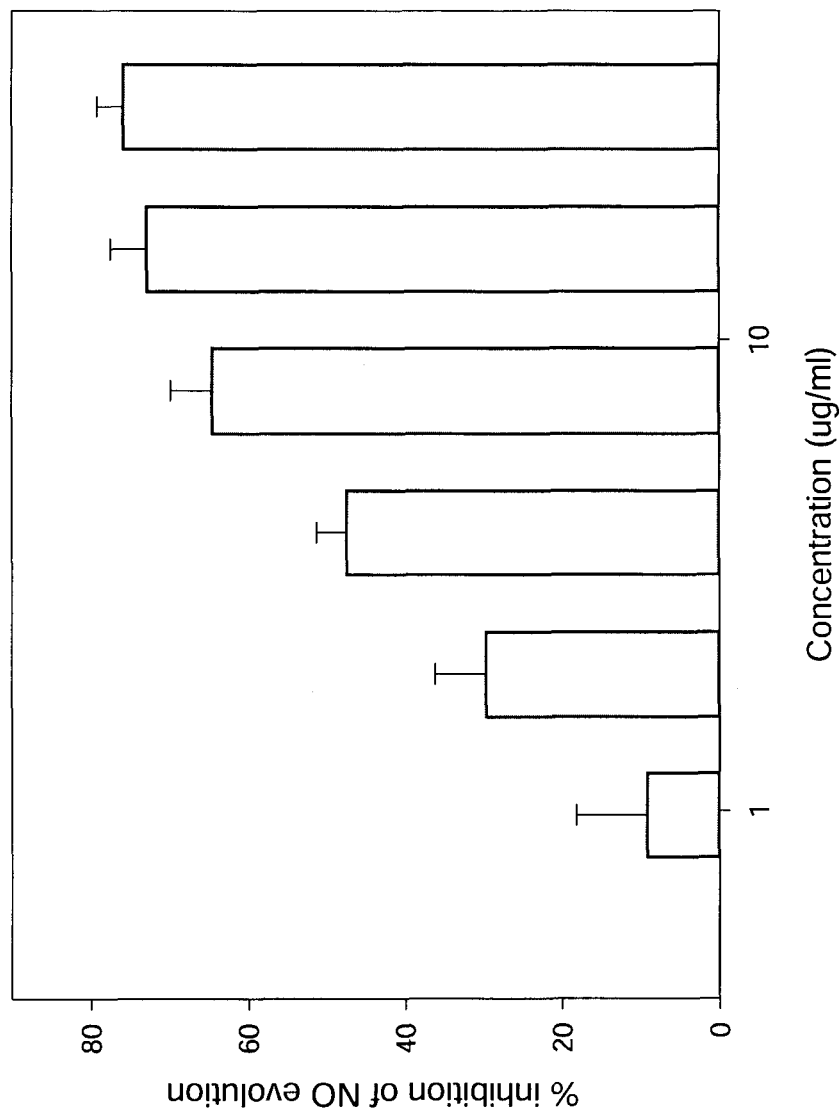
FIG. 12 depicts the inhibition of NO evolution by GSSPe in RAW 267.4 cells as analyzed in Example 28.

Specifically, the anti-inflammatory activity of the mixed disulfide conjugates prepared in Example 14 using the murine macrophage cell line (RAW 264.7) and established procedures for measuring the inhibition of nitric oxide (NO) in lipopolysaccharide (1 μg/ml)-activated macrophages (Kim, et al., 2003) was analyzed. Each conjugate was tested over a dose range and the evolution of NO over the 24 hour incubation period was measured as nitrate by the Griess reagent using established protocols (Granger et al., 1996). The dose where a 50% inhibition of NO evolution occurred ($IC_{50}$) relative to the control cells without added conjugate was estimated by sigmoidal curve-fitting as a relative measure of anti-inflammatory activity, with lower $IC_{50}$ values representing greater potency. Results were obtained where cell viability was ≧80% under the conditions evaluated. Typical experimental results are shown for the GSSPe conjugate (FIG. 12), and summary results are provided for all conjugates in terms of relative potency ($IC_{50}$ values) for NO inhibition (Table 9). All mixed disulfide conjugates inhibited NO evolution with the unsaturated species of conjugates being more potent that saturated species, and with CySSR species being generally more potent than GSSR species on a molar concentration basis.

TABLE 9

NO inhibition by in activated macrophages CYS and GSH conjugates of thiosulfinates (CySSR/GSSR).

| Compound | $IC_{50}$ values (μg/ml) | (μM) |
|---|---|---|
| CySSM | 48 | (290) |
| CySSE | 102 | (560) |
| CySSP | 63 | (320) |
| CySSPe | 21 | (110) |
| CySSA | 9 | (47) |
| di-1-propenyl derivatives** | 15 | NA |
| GSSM | *NA | — |
| GSSE | *NA | — |
| GSSP | *NA | — |
| GSSPe | 4.6 | (16) |
| GSSA | 87 | (230) |

*NA indicates not applicable: GSSM, GSSE and GSSP respectively caused 26%, 25% and 34% inhibition of NO evolution at 125 μg/ml, the highest level tested.
**Prepared as in Example 7. These were not pure, so there was no μM equivalent that could be estimated, and they were not conjugated with either CYS or GSH.

EXAMPLE 28

In this Example, the oxidation-reduction (redox) modulation and thiol upregulation activity was assessed for the mixed disulfide conjugates prepared in Example 11.

Generally, redox modulation and thiol upregulation is considered a defense mechanism to pathological processes in cells. These mechanisms were analyzed in the mixed disulfide conjugates in both Hepa 1c1c7 and RAW 264.7 macrophage cell lines. Evidence of redox modulation was obtained in terms of 1) attenuation of QR inducing activity with increasing reducing capacity of cells through exogenous GSH addition, 2) increases in cellular glutathione (GSH) and 3) export/enrichment of thiols in the extracellular fluid.

Figure 13:
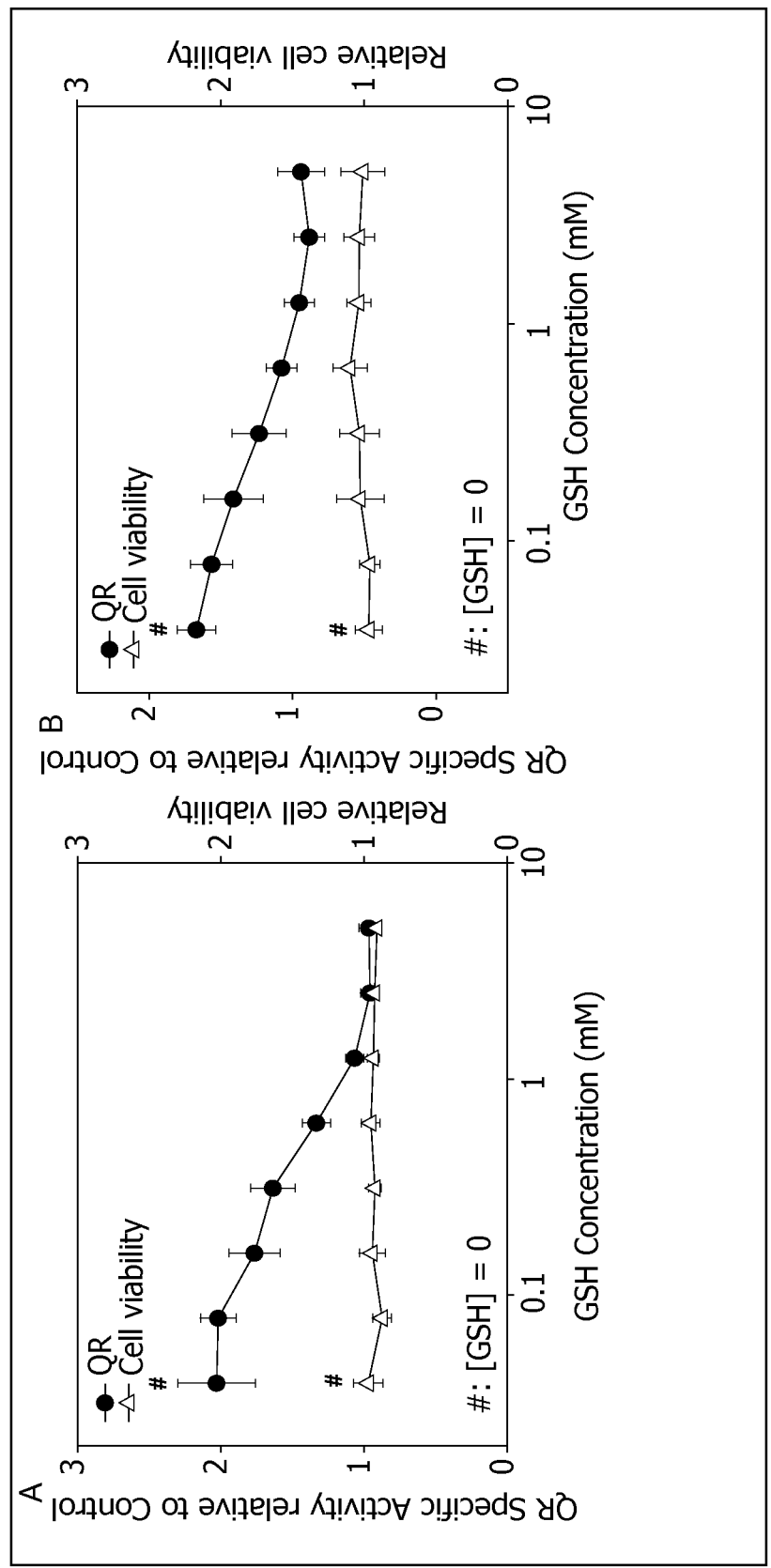
FIG. 13 depicts the attenuation of QR inducing effect by CySSA and GSSA in the presence of exogenous GSH in Hepa 1c1c7 cells as analyzed in Example 29.

The addition of 31 μg/ml CySSA and GSSA caused nearly a doubling of QR in Hepa 1c1c7 cells, but this induction was progressively attenuated when increasing levels of exogenous GSH were added to the medium (FIG. 13). This shows that the conjugates exert their biological effects in part by imposing a mild oxidative stress on the cells, to which the cells respond by elevating antioxidant defense systems. The addition of exogenous GSH artificially enhanced the reducing capacity of the cells and counteracted the redox stress imposed by the conjugates, thereby reducing the biological effect on NO evolution.

Another related consequence of adding the conjugates to the cells was an increase in cellular GSH. This response is considered to be a general antioxidant defense as well as one that provides specific protection to cancer (Kim et al., 2009) and was assessed in the next Example.

EXAMPLE 29

In this Example, GSSP was added to Hepa 1c1c7 cells and changes in intracellular GSH content were measured.

Figure 14:
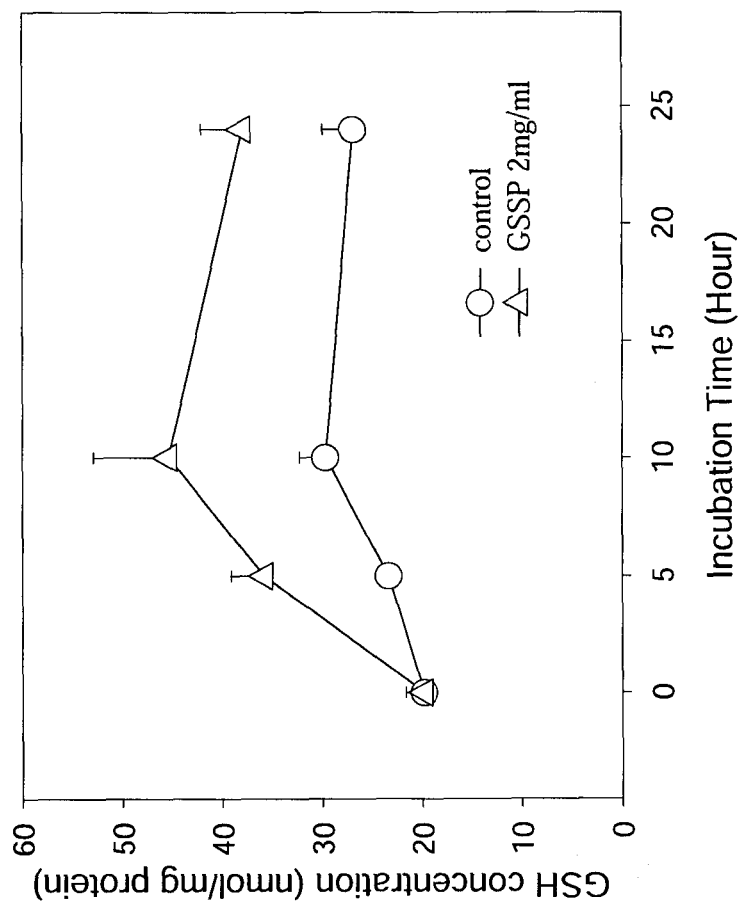
FIG. 14 depicts the GSH levels in GSSP-treated and control Hepa 1c1c7 cells as analyzed in Example 30.

Specifically, GSSP was prepared similar to the GSSR conjugates in Example 11 and added to Hepa 1c1c7 cells. The changes in intracellular GSH content was measured after lysis of the cells at pre-determined intervals after addition of the GSSP conjugate. GSH was elevated in GSSP-treated cells by 50-70% over the first 10 hours (FIG. 14), indicating that this conjugate could upregulate glutathione synthesis in cells.

EXAMPLE 30

In this Example, the effect on cellular efflux of thiols by macrophages having various CySSR or GSSR species was analyzed.

Figure 15:
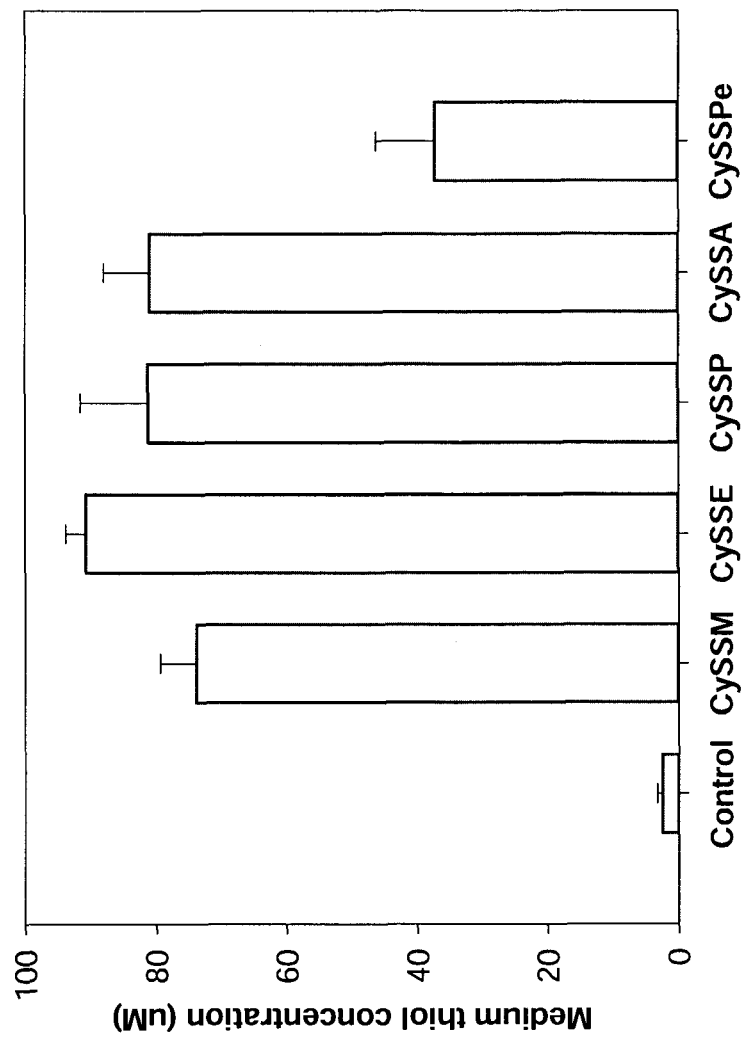
FIG. 15 depicts the extracellular thiol concentrations of RAW 264.7 cells treated with CySSR and 5,5'-dithio-bis(2-nitrobenzoic acid) (DTNB) as analyzed in Example 31.

Specifically, CySSR as prepared in Example 11 was added to macrophages. Thiol export by the macrophages was then analyzed. All CySSR species tested at 31 μg/ml induced thiol export by macrophages by as much as 20-35 times level observed for untreated control cells. Thiols were measured by Ellman's reagent (DTNB). Typical results revealed little difference between CySSR species, except that CySSPe caused about half as much thiol efflux as the others (FIG. 15). Cellular exporting of thiols represents another mechanism by which cells respond to oxidative stress by exporting reducing equivalents to restore extracellular redox homeostasis. GSSR species only marginally increased extracellular thiols over levels of control cells, indicating that GSSR and CySSR species differ in some respects in their biological effects on cells related to redox modulation.

What is claimed is:

1. A process for preparing mixed disulfide conjugates from *Allium* organosulfur compounds, the process comprising:
    homogenizing an allinase-bearing tissue source; contacting the homogenate with a source of S-alk(en)yl-L-cysteine sulfoxides (ACSO) under suitable conditions to produce a mixture of thiosulfinates; and
    reacting the mixture of thiosulfinates with a thiol component under suitable conditions to produce the mixed disulfide conjugates,
    wherein the thiol component is selected from the group consisting of cysteine, glutathione, peptides, protein hydrolysates, and proteins.

2. The process as set forth in claim 1 wherein the allinase-bearing tissue source is derived from garlic, chives, leeks, onions, *Brassica* spp., spinach, Shitake mushroom, *Tulbaghia violacea, Albizzia lophanta, Penicillium corymbiferum, Pseudomonas* spp., *Bacillus subtilis, Acacia farnesiana*, and mixtures thereof.

3. The process as set forth in claim 1 wherein the alliinase-bearing tissue source is homogenized at ambient temperature within the range of from about 0° C. to about 40° C.

4. The process as set forth in claim 1 further comprising extracting the homogenate in a water-immiscible solvent at ambient temperature for a time period sufficient to extract nascent thiosulfinates that form in the homogenate.

5. The process as set forth in claim 1 wherein the source of ACSO is a natural or synthetic source of ACSO, wherein the synthetic source of ACSO is selected from the group consisting of (+)-S-Methyl-L-cysteine sulfoxide (MCSO); (+) -S-ethyl-L-cysteine sulfoxide (ECSO); (+)-S-propyl-L-cysteine sulfoxide (PCSO); (+)-S-1-propenyl-L-cysteine sulfoxide (1-PeCSO); and (+)-S-2-propenyl-L-cysteine sulfoxide (2-PeCSO).

6. The process as set forth in claim 1 wherein the source of ACSO is treated to inactivate any endogenous lachrymatory factor synthase (LF synthase) activity prior to being contacted with the homogenate.

7. The process as set forth in claim 1 wherein the thiosulfinates produced have a structure of the general formula:

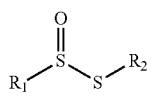

wherein $R_1$ and $R_2$ are independent selected from the group consisting of alkyl, alkenyl, and mixtures thereof.

8. The process as set forth in claim 1 wherein the thiosulfinates produced are selected from the group consisting of:

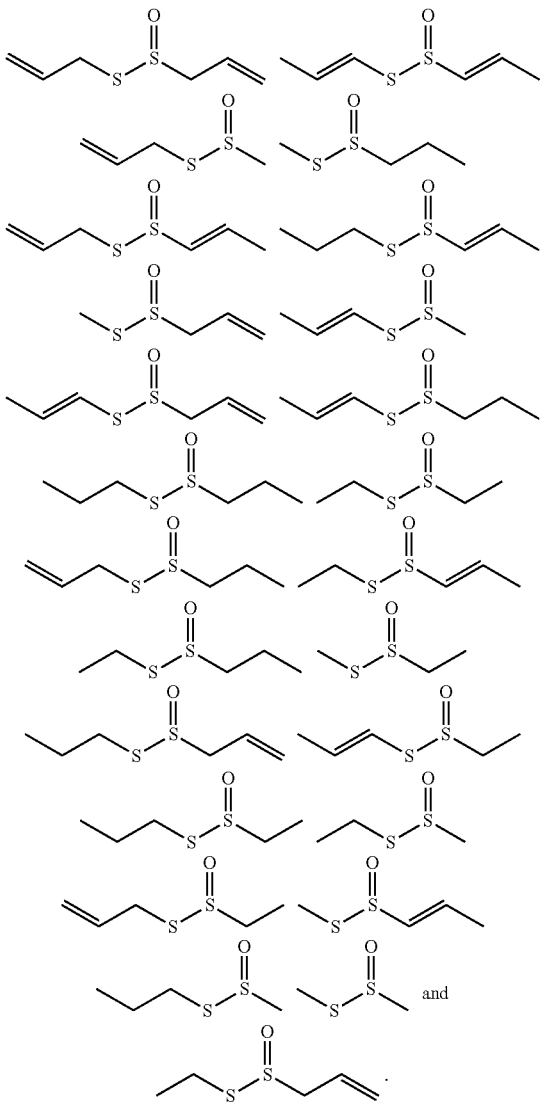

9. The process as set forth in claim 1 further comprising purifying the mixture of thiosulfinates prior to reacting the mixture.

10. A process for preparing mixed disulfide conjugates from *Allium* organosulfur compounds, the process comprising:
    homogenizing an alliinase-bearing tissue source;
    contacting the homogenate with a source of S-alk(en)yl-L-cysteine sulfoxides (ACSO) under suitable conditions to produce a mixture of thiosulfinates; and
    reacting the mixture of thiosulfinates with a thiol component under suitable conditions to produce the mixed disulfide conjugates, wherein the thiol component is selected from the group consisting of proteins and protein hydrolysates.

11. The process as set forth in claim 10, wherein the protein is selected from the group consisting of keratin, whey protein isolate, soy protein isolate, egg white protein, and combinations thereof.

12. The process as set forth in claim 10 wherein the allinase-bearing tissue source is derived from garlic, chives, leeks, onions, *Brassica* spp., spinach, Shitake mushroom,

*Tulbaghia violacea, Albizzia lophanta, Penicillium corymbiferum, Pseudomonas* spp., *Bacillus subtilis, Acacia farnesiana*, and mixtures thereof.

13. The process as set forth in claim 10, wherein reacting the mixture of thiosulfinates with the thiol component wherein the mixture comprises a molar ratio of thiosulfinates to thiol component of from about 1:2 to about 10:1.

* * * * *